United States Patent
Berry et al.

(10) Patent No.: US 8,062,303 B2
(45) Date of Patent: Nov. 22, 2011

(54) APPARATUS AND METHODS FOR INSERTING AN IMPLANT

(75) Inventors: Bret M. Berry, Sandy, UT (US); Richard D. Guyer, Dallas, TX (US); Jack E. Zigler, Dallas, TX (US); Adam A. Pike, Bountiful, UT (US); Randall F. Lee, Arlington, TX (US)

(73) Assignee: K2M, Inc., Leesburg, VA (US)

( * ) Notice: Subject to any disclaimer, the term of this patent is extended or adjusted under 35 U.S.C. 154(b) by 971 days.

(21) Appl. No.: 11/622,545

(22) Filed: Jan. 12, 2007

(65) Prior Publication Data
US 2008/0275455 A1 Nov. 6, 2008

Related U.S. Application Data

(60) Provisional application No. 60/822,613, filed on Aug. 16, 2006.

(51) Int. Cl.
*A61B 17/58* (2006.01)
*A61B 17/60* (2006.01)
*A61B 1/32* (2006.01)
*A61F 5/00* (2006.01)

(52) U.S. Cl. ............................. 606/90; 606/99; 600/219

(58) Field of Classification Search ................ 606/86 A, 606/86 B, 99, 104, 90; 600/221, 222, 219
See application file for complete search history.

(56) References Cited

U.S. PATENT DOCUMENTS

| | | | |
|---|---|---|---|
| 3,486,505 A | 12/1969 | Morrison | |
| 3,762,400 A * | 10/1973 | McDonald | 600/212 |
| 4,714,469 A | 12/1987 | Kenna | |
| 5,122,130 A * | 6/1992 | Keller | 606/86 A |
| 5,431,658 A | 7/1995 | Moskovich | |
| 5,571,109 A | 11/1996 | Bertagnoli | |
| 5,599,279 A | 2/1997 | Solomon et al. | |
| 5,683,399 A * | 11/1997 | Jones | 606/91 |
| 6,159,215 A | 12/2000 | Urbahns | |
| 6,478,800 B1 | 11/2002 | Fraser et al. | |

(Continued)

FOREIGN PATENT DOCUMENTS

EP 0637439 A1 2/1995

(Continued)

OTHER PUBLICATIONS

Synthes, Inc. "Luminary ALIF. Disc preparation and implant insertion instruments" pp. 1-23, 2006.

*Primary Examiner* — Thomas C. Barrett
*Assistant Examiner* — David Bates
(74) *Attorney, Agent, or Firm* — Matthew B. Dernier, Esq.; Gibson & Dernier LLP

(57) ABSTRACT

A system and method for inserting an implant into a cavity is disclosed, which may include advancing an implant insertion instrument toward a pair of adjacent bodies, the implant insertion instrument having two opposed ramps, wherein each ramp has a distal tip and wherein the longitudinal axes of the opposed ramps are separated by an initial angle; inserting the distal tips of the opposed ramps between the adjacent bodies, thereby creating an initial interbody cavity between the adjacent bodies; expanding the interbody cavity while maintaining the initial angle between the longitudinal axes of the opposed ramps; placing the implant in a final location between the adjacent bodies; transferring a compressive force urging the adjacent bodies together from the opposed ramps to the implant; and extracting the implant insertion instrument from the interbody cavity.

22 Claims, 20 Drawing Sheets

U.S. PATENT DOCUMENTS

| | | |
|---|---|---|
| 6,569,168 B2 | 5/2003 | Lin |
| 6,616,671 B2 | 9/2003 | Landry et al. |
| 6,652,533 B2 | 11/2003 | O'Neil |
| 6,755,841 B2 | 6/2004 | Fraser et al. |
| 6,770,074 B2 | 8/2004 | Michelson |
| 6,824,565 B2 | 11/2004 | Muhanna et al. |
| 6,887,248 B2 | 5/2005 | McKinley |
| 6,986,772 B2 | 1/2006 | Michelson |
| 7,070,598 B2 * | 7/2006 | Lim et al. ............... 606/99 |
| 7,087,055 B2 | 8/2006 | Lim et al. |
| 7,204,852 B2 | 4/2007 | Marnay |
| 7,294,134 B2 * | 11/2007 | Weber ............... 606/99 |
| 7,608,078 B2 * | 10/2009 | Berry ............... 606/86 A |
| 7,625,377 B2 * | 12/2009 | Veldhuizen et al. ....... 606/90 |
| 7,625,379 B2 | 12/2009 | Puno et al. |
| 7,896,884 B2 * | 3/2011 | Wing et al. ............... 606/90 |
| 2002/0116009 A1 | 8/2002 | Fraser et al. |
| 2003/0055434 A1 | 3/2003 | O'Neil |
| 2004/0030346 A1 * | 2/2004 | Frey et al. ............... 606/99 |
| 2004/0066884 A1 | 8/2004 | De Villiers |
| 2004/0225295 A1 | 11/2004 | Zubok |
| 2004/0267277 A1 | 12/2004 | Zannis et al. |
| 2005/0021042 A1 | 1/2005 | Marnay et al. |
| 2005/0113842 A1 | 5/2005 | Bertagnoli et al. |
| 2005/0143747 A1 * | 6/2005 | Zubok et al. ............... 606/90 |
| 2005/0165408 A1 | 7/2005 | Pino et al. |
| 2005/0182416 A1 | 8/2005 | Lim et al. |
| 2006/0030856 A1 * | 2/2006 | Drewry et al. ............... 606/90 |
| 2006/0030857 A1 | 2/2006 | de Villiers |
| 2006/0052793 A1 * | 3/2006 | Heinz ............... 606/90 |
| 2006/0122701 A1 * | 6/2006 | Kiester ............... 623/17.11 |
| 2006/0241641 A1 | 10/2006 | Albans |
| 2006/0241643 A1 | 10/2006 | Lim et al. |
| 2007/0016220 A1 | 1/2007 | Michelson |
| 2007/0191857 A1 | 8/2007 | Allard et al. |
| 2008/0161817 A1 * | 7/2008 | Parsons et al. ............... 606/90 |
| 2010/0069914 A1 | 3/2010 | Puno et al. |
| 2010/0249792 A1 * | 9/2010 | Bonvallet et al. ............... 606/90 |

FOREIGN PATENT DOCUMENTS

| | | |
|---|---|---|
| EP | 1295578 A2 | 3/2003 |
| EP | 1323396 A2 | 7/2003 |
| WO | 2004066884 A1 | 8/2004 |
| WO | 2005072662 A1 | 8/2005 |

* cited by examiner

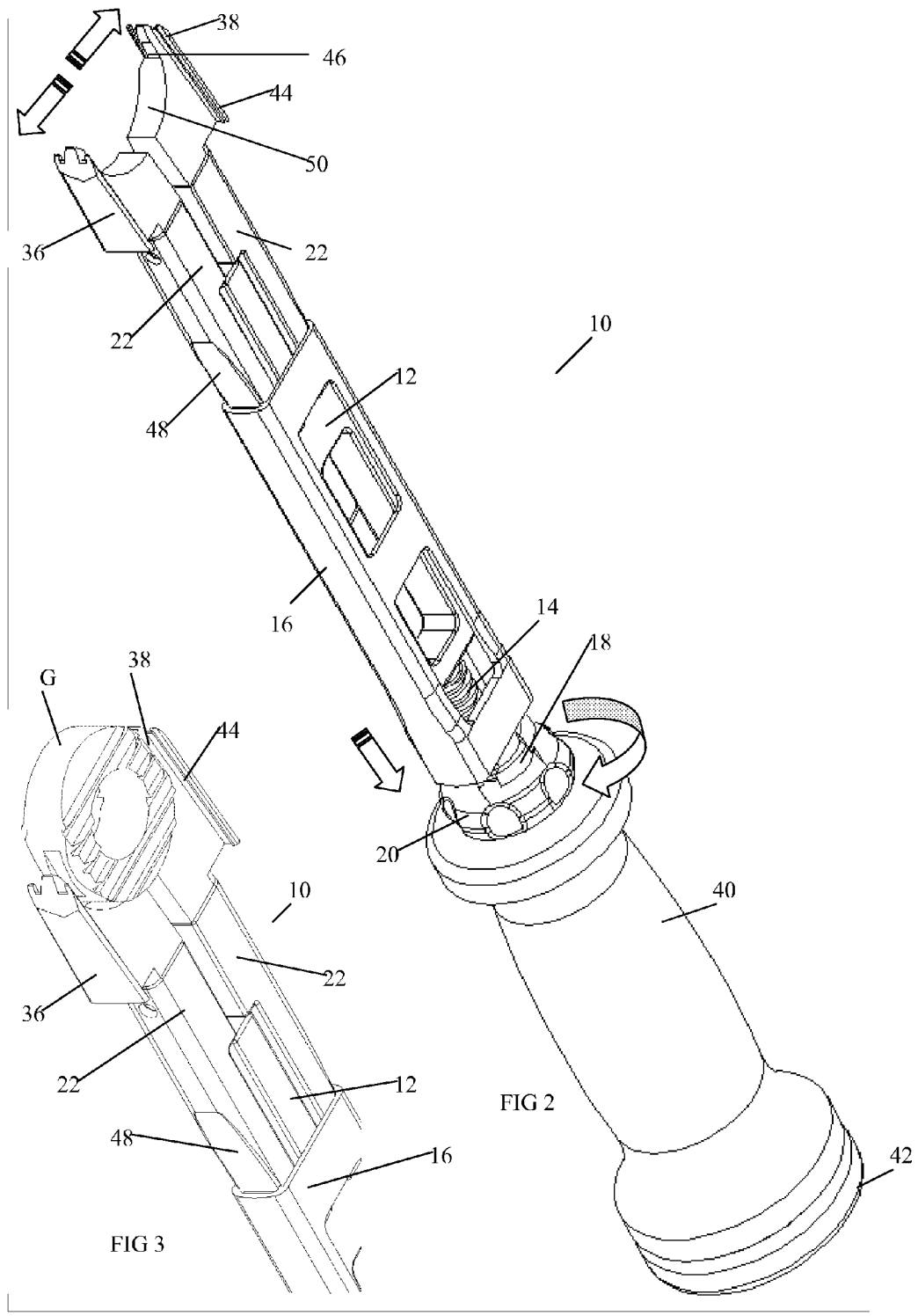

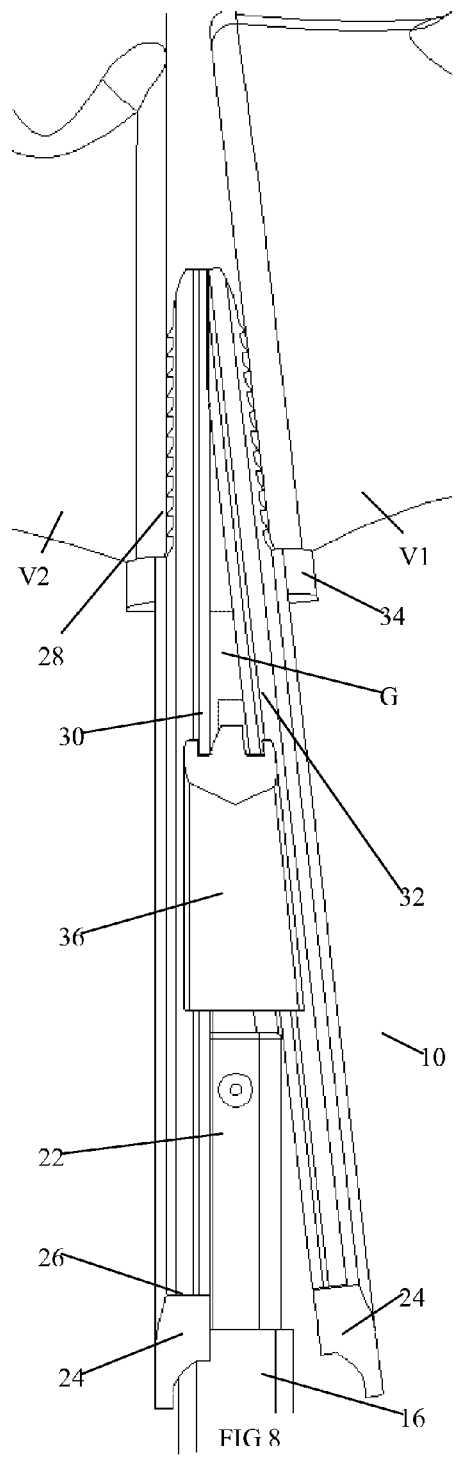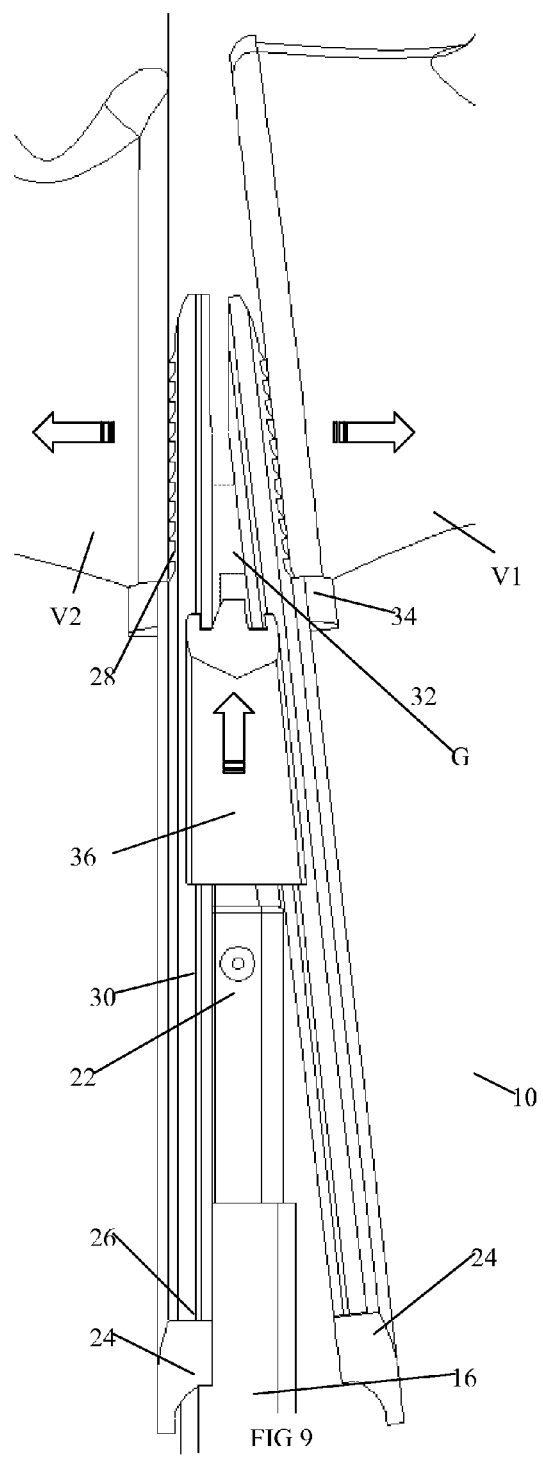

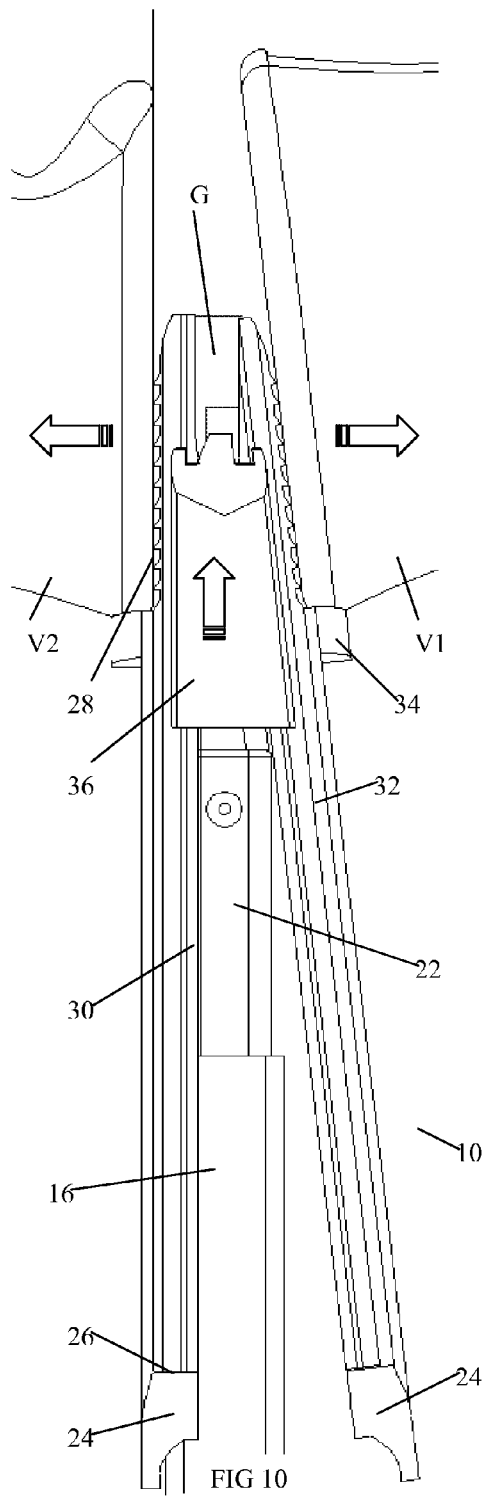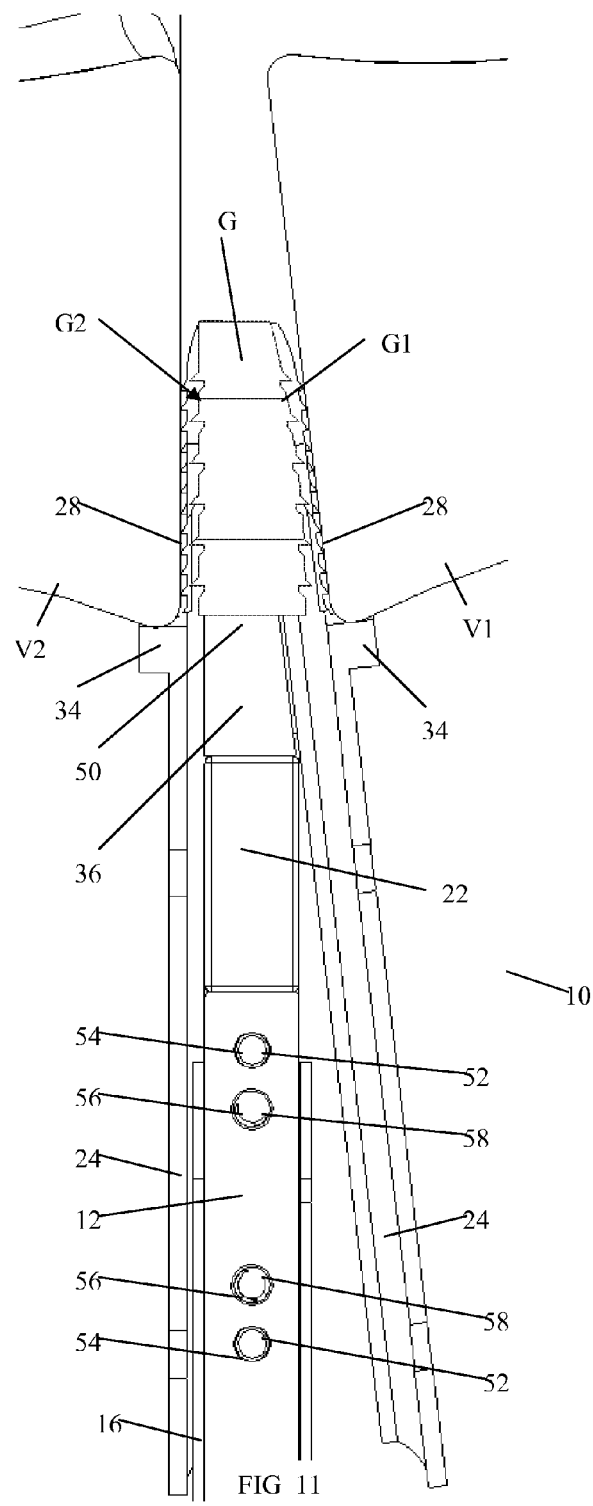

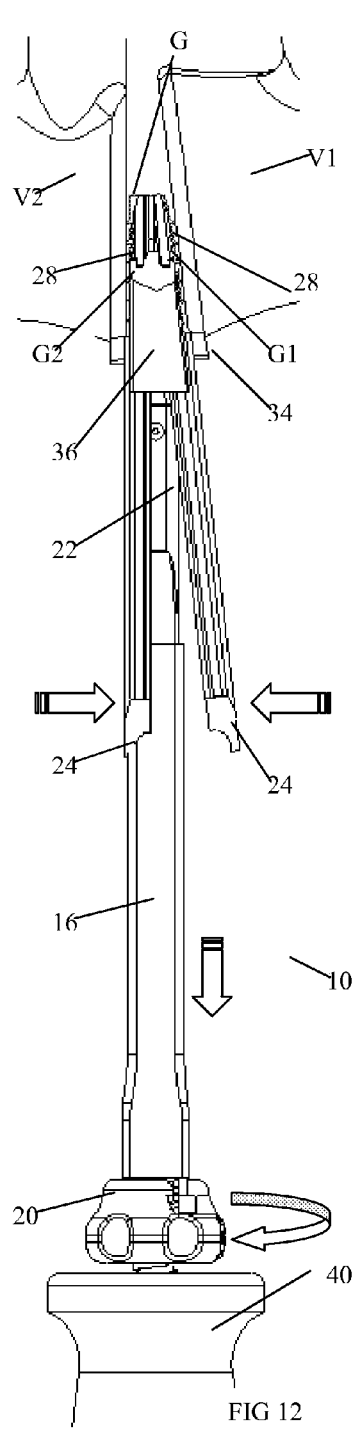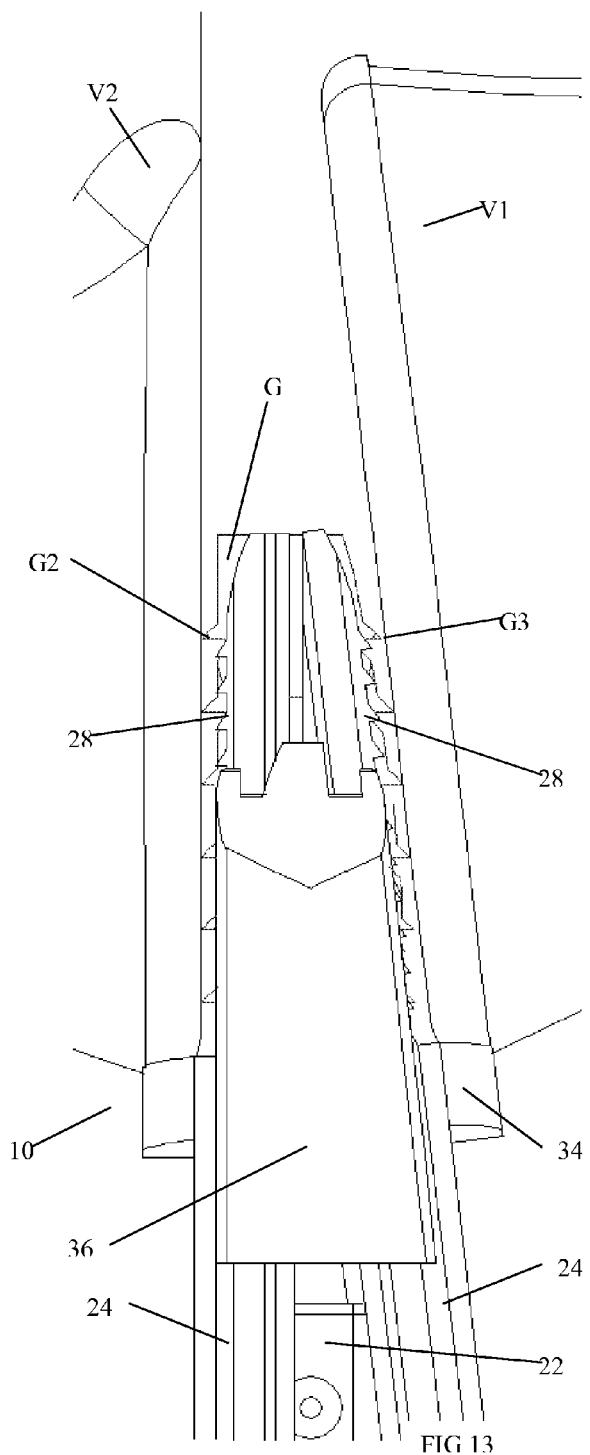
FIG 12
FIG 13

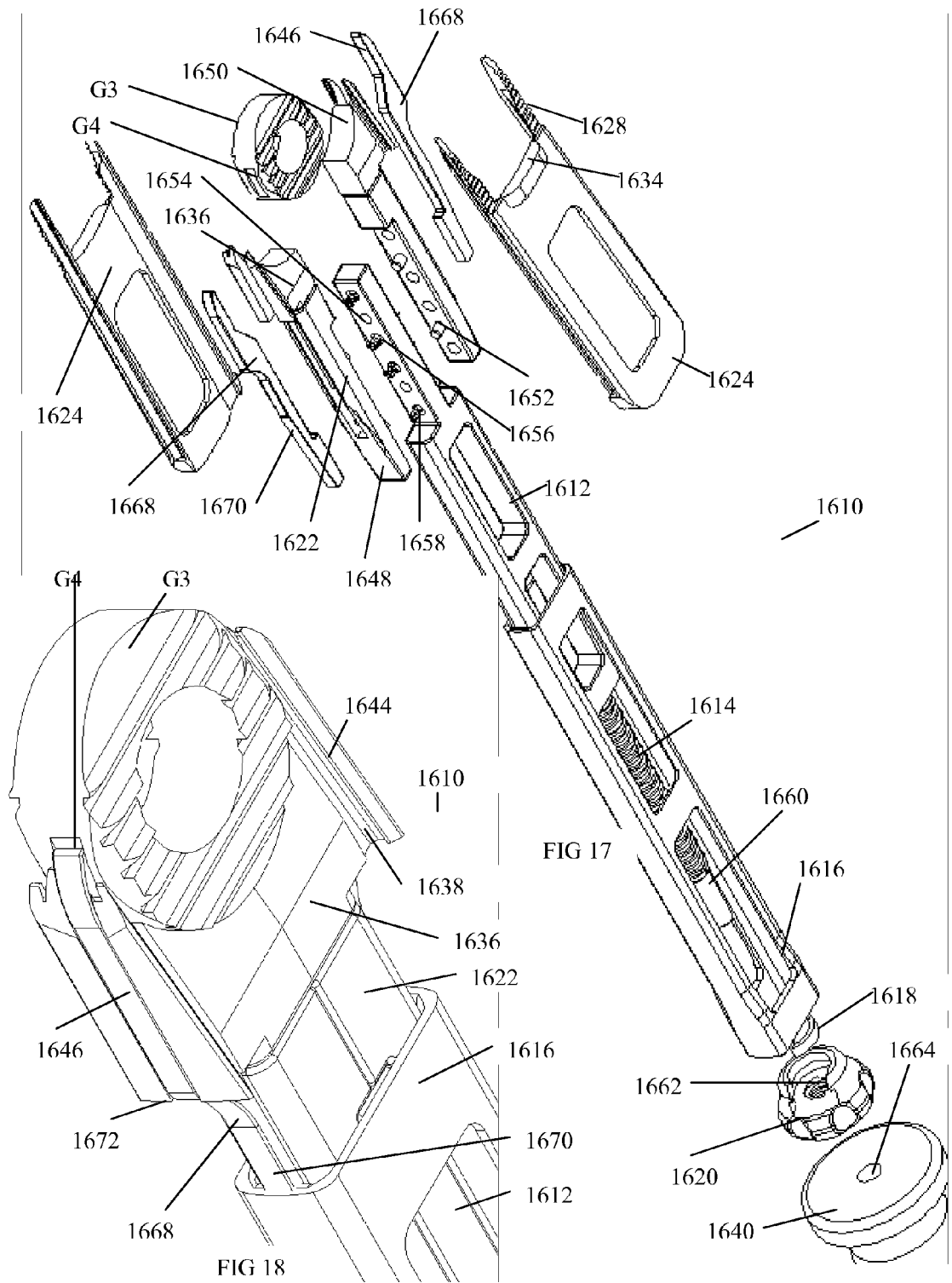

APPARATUS AND METHODS FOR INSERTING AN IMPLANT

CROSS REFERENCE TO RELATED APPLICATIONS

This application claims the benefit of U.S. Provisional Patent Application No. 60/822,613 filed Aug. 16, 2006, the entire disclosure of which is hereby incorporated by reference.

BACKGROUND OF THE INVENTION

This present invention is directed to methods and apparatus for interbody distraction and implant/transplant insertion.

The spine surgical community and surgical literature accept intervertebral devices (commonly known as interbody spacers, and allograft transplants) as part of the art and routine practice in the reconstruction of collapsed intervertebral disc spaces. Surgeons insert these interbody devices/transplants to facilitate bone fusion in between and into the contiguous involved vertebrae. This fusion creates a new solid bone mass, which acts to hold the spinal segment at an appropriate biomechanically restored height as well as to stop motion in a painful segment of the spine. Items surgically placed in these involved interbody regions can thus stimulate interbody bone in-growth such that the operated anterior spinal segments heal into a contiguous bone mass; this means that a fusion occurs. Further, the surgical community uses such man-made implants or biological options to provide weight bearing support between adjacent vertebral bodies, and thereby correct or alleviate a variety of clinical problems. In this regard, surgeons use intervertebral spinal implants/transplants for surgical therapy for degenerative disc disease (DDD), discogenic low back pain, spondylolisthesis, reconstruction following tumor or infection surgery, and other spine related maladies requiring surgical intervention. Herein, a gap separating two adjacent bodies is referred to as an interbody cavity. A gap separating two adjacent vertebral bodies is referred to as an intervertebral cavity.

In many implant designs, a relatively hard or sturdy implant construct is formed from a selected biocompatible material such as metal, ceramic, or carbon fiber-reinforced polymer. This implant construct often has a partially open or porous configuration and is coated or partially filled with a selected bone ingrowth-enhancing substance, such as harvested bone graft supplied from the patient, human donor allograft bone transplant material supplied by a tissue bank, genetically cultivated bone growing protein substitutes, and/or other biological/biochemical bone extenders. Such devices, when implanted into the intervertebral space, promote ingrowth of blood supply and grow active and live bone from the adjacent spinal vertebrae to inter-knit with the implant, thereby eventually immobilizing or fusing the adjacent spinal vertebrae. Such implants also commonly include a patterned exterior surface such as a ribbed or serrated surface, or screw thread geometry, to achieve enhanced mechanical locking with the adjacent vertebrae during the bone ingrowth/fusion process.

The inventory of available surgical devices has expanded to include machined, transplantable allograft bone spacers. Bone Banks and tissue processors are able to precision-engineer donated human bone to specific vertebral interbody milled dimensions most likely to fit into the affected intradiscal zones. For many spine surgeons these biological solutions may prove a better option for a particular patient than the use of man-made materials.

The intervertebral or interbody implants of these general types have achieved a significant degree of clinical success. Notwithstanding this success, a variety of problems arise in connection with surgical interbody implant placement. Surgeons can have difficulty with the implantation process because of individual pathology, deformity, anatomical space restraints, or implant material limitations.

Often, implant placement proves a difficult and time-consuming procedure when the adjacent vertebrae's soft tissue support elements degenerate, causing collapse of the spaces between the vertebrae. This degenerative condition coupled with compromised adjacent tissues, nerves and vasculature may impede physical and visual access to the intervertebral space.

Spine surgery of this type may require removal of the remaining disc material, release of the contracted soft tissues around the disc space, and some degree of distraction or pulling apart of the adjacent vertebrae in an attempt to restore disc space height, realign the spine, and indirectly decompress the nerve roots exiting the spine posteriorly at that level. This distraction procedure has traditionally required the use of several surgical distraction instruments, which may increase the procedure's overall complexity, intensify the invasiveness of the surgical procedure, and possibly lead to iatrogenic vascular and neurosurgical injuries which can cause intraoperative surgical complications. At the same time, use of multiple instruments may limit the surgeon's manual access and clear visualization of the involved intervertebral space.

After the surgeon removes the disc material, he has made a clean aperture in which to place the device. Typically the surgeon grasps the interbody spacer with a special pliers-like tool and places it at the mouth of this opening. At this juncture, the surgeon typically uses extreme force as he hammers on the top part of the tool so that the implant finds its final placement. This hammering technique vectors enormous shear forces through the spacer. The actual implants have material and engineering limitations which may cause the implant to fracture, shear, or break apart as a result of these forceful insertion moments. In addition, some implant designs require materials which do not tolerate well the use of impaction-type forces necessary to advance the implant into the intervertebral space.

A variety of intervertebral implant insertion instruments have been developed in recent years as a result of efforts to simplify surgical distraction of the intervertebral space while facilitating placement of the implant therein. See, for example, U.S. Pat. Nos. 6,755,841; 6,478,800; and 6,652,533; and U.S. Publication No. 2005/0165408 which disclose instruments for advancing an intervertebral implant between a pair of pivotally mounted distraction levers used to engage and distract adjacent vertebral structures. In these designs, the advancing movement of the implant is accompanied by wedged separation of the distal end tips of the levers which are engaged with and thereby separate or distract the adjacent vertebral structures.

While such implant insertion instruments provide a significant improvement in the art, the implant is not always safeguarded against substantial and potentially undesirable compression and shear forces during such advancing displacement between the pivoting distraction levers. In addition, these instruments have not provided a simple mechanism for quickly and easily retracting the distal end tips of the levers from the distraction space following intervertebral placement of the implant. Moreover, these instruments have not provided or contemplated the capability for use with implants of different sizes, such as implants having different height dimensions which may be indicated by specific patient requirements, without altering the insertion angle of the distal end tips of the distraction levers. In this regard, an amplified increase in the tip insertion angle, associated with implantation of a significantly taller implant, can undesirably increase the complexity and difficulty of the surgical implantation procedure.

There exists, therefore, a significant need for further improvements in and to intervertebral implant insertion instruments and related intervertebral implants for use therewith, particularly with respect to quickly and easily distracting the intervertebral space for facilitated placement of an implant having a range of different heights, for safeguarding the implant against compression and shear forces during intervertebral distraction, and further for quickly and easily releasing the implant from the insertion instrument within the intervertebral space.

SUMMARY OF THE INVENTION

According to one aspect, the present invention provides: an instrument for inserting an implant which may include at least two opposed ramps having an initial angle between the respective longitudinal axes thereof, each ramp having a proximal and a distal end; at least one distraction guide disposed between the opposed ramps and mobile with respect to the ramps along the longitudinal axes thereof, wherein advancement of the distraction guide distally along the longitudinal axes of the ramps is operable to separate the ramps while holding the initial angle between the two ramps at least substantially constant.

According to another aspect, the present invention provides a method for inserting an implant into a cavity which may include advancing an implant insertion instrument toward a pair of adjacent bodies, the implant insertion instrument having two opposed ramps, wherein each ramp has a distal tip and wherein the longitudinal axes of the opposed ramps are separated by an initial angle; inserting the distal tips of the opposed ramps between the adjacent bodies, thereby creating an initial interbody cavity between the adjacent bodies; expanding the interbody cavity while maintaining the initial angle between the longitudinal axes of the opposed ramps; placing the implant in a final location between the adjacent bodies; transferring a compressive force urging the adjacent bodies together from the opposed ramps to the implant; and extracting the implant insertion instrument from the interbody cavity. The distraction guide and ramp may be provided as separate parts that may be reversibly assembled to one another as needed. Alternatively, a module including one or more distraction guides and one or more ramps may be provided as a substantially permanent assembly.

One or more embodiments of the invention have applicability when a spine surgical team access the spine from a retro peritoneal or anterior lateral approach. The spine surgeon may initially remove disc material from the anterior or anterior lateral involved disc space, and may then insert an instrument embodying one or more aspects of the invention between two human spinal vertebrae to distract or separate the opposing vertebrae. The surgeon may then place a spinal implant and or allogenic transplant of specific dimensions and geometry into the opened intervertebral space. One or more aspects of the invention may be directed to an instrument having novel ramp segments for safe and reliable distraction of the bone structures in a manner accommodating a range of different implant and transplant sizes. Thus, an instrument in accordance with one or more embodiments of the present invention may be employed to gently insert the intervertebral device or transplant safely and with relatively little force.

In accordance with one or more aspects of the invention, an improved insertion instrument that may be placed through an anterior or anterior lateral surgical wound, may operate to distract adjacent bony structures, such as spinal vertebrae, and to insert an implant into the distracted and evacuated disc space. The insertion instrument may include an elongated inserter body having a modular and a removable distal end that may be coupled to a distraction guide which may include a pair of clamp jaw components with tall side walls that may be configured to support, carry, grasp and/or thread into, and release the implant, in combination with a pair of sliding trapezoidal ramped wedges that may be mounted into the distraction guides so that as the wedges travel along the guide, the wedges may engage and distract the device and consequently distract the adjacent spinal vertebrae or like structures. The side walls of the distraction guides, which may be tall, may have elongated grooves cut at an angle corresponding to the angle of the cephalad and caudal faces of the implant. In one or more embodiments, the grooves may have a first portion which may be perpendicular to the side walls and/or a second portion which may be at an non-perpendicular angle relative to the side wall, thus forming a "figure 4" type shape. This groove may extend from the proximal end to the distal end of the distraction guide. In one or more embodiments, the side walls of the distraction guide may define a height dimension slightly less than a corresponding height dimension of the implant carried thereby.

In one or more embodiments, the distal end of the inserter body may be adapted to enable removable mounting of the distraction guide including the clamp jaw components of selected size and shape for supporting and retaining the implant. Likewise, one or more further embodiments of the device may use a threaded rod placed through the center of the implant delivery handle that is designed to engage or mate to a threaded hole found anteriorly or off axis through the implants. Likewise, one or more further embodiments of the device may use non threaded prominences (protrusions) placed centrally on the jaw components or along the radius of the clamp jaws that are designed to engage or mate through the implants to non threaded holes, slots, grooves found anteriorly, anterior laterally or other possible off axis interfaces into or through the implant/transplant. In one or more embodiments, the inserter body and jaw components may define a keyed interlock assembly. The jaw components may be carried by arm members that are mounted so as to slide from the proximal to distal instrument ends onto the inserter body and may be spring loaded such that default displacement may be directed in a laterally outward direction, thereby spreading the jaw components sufficiently for to release the implant. In one or more embodiments, the arm members may be retained in a laterally inboard position by a tube mechanism for normal clamp-lock retention of the implant. In one or more embodiments, the tube mechanism may include a square surface attached to a threaded member that may be engaged at the distal end. This threaded member may be engaged with an external thread at the distal end of the inserter body. As the threaded member rotates, the sliding mounted tube mechanism may move along the exterior of the inserter body and the arm members. In one or more embodiments, the arm members have angled faces on their outward surfaces, such that the angled faces may be engaged by the interior surface of the tube member, thereby allowing the arm members to be forced in and out, depending on the position of the tube member. In one or more embodiments, when the tube member is in the proximal position, the arm members may be pressed outward by the internal springs, thus releasing the implant. However, when the threaded member is moved to a more distal position, the corresponding clamp jaw components may be forced inward, thereby supporting and retaining the implant.

In one or more embodiments, the distal-end ramp segments of the two distraction ramps may include distal-end distraction tips shaped to fit between adjacent spinal vertebrae. The distraction guides may be advanced between the ramps to distract the distal-end ramp segments and the vertebral structures engaged thereby, and also advance the implant into the resulting distracted intervertebral space. The distraction guide(s) may define a height dimension slightly less than the thickness of the implant being advanced by the guides. However, the distraction guide may cooperate with the distal-end ramp segments to provide a combined height dimension that is slightly greater than the implant height to prevent compression and shear force loading of the implant during advancement thereof between the distraction ramps. The outer surfaces of the distal-end ramp segments may be roughened or serrated in a manner that may be effective to grip the adjacent endplates of the vertebral bodies in order to prevent movement of the ramps in relation to the bone. Furthermore, an elongated groove extending from the distal ends of the ramps to the point just offset from the proximal ends of the ramps may be located on each of the outer lateral walls of the ramps. These grooves may include a first portion which may be perpendicular to the side walls and a second portion which may be oriented at an angle relative to the side wall, thus forming a "figure 4" type shape. The above-described ramp grooves may have an orientation opposite those which may be present on the interior side walls of the distraction guides. The grooves on the ramps may engage the grooves on the distraction guides, thereby enabling the ramps to slide with respect to the distraction guides.

In one or more embodiments, the above described geometric interface between the ramps and the distraction guides may operate to transfer the compressive force load from the vertebral bodies through the ramps and onto the distraction guides. The preferably perpendicular portion of the groove may enable the ramps to slide along the distraction guides while maintaining a specific lordotic angle throughout the insertion process. In one or more embodiments, the endplates of the vertebral bodies may be held at this specified lordotic angle while being distracted axially during the implantation. With the tube mechanism in the distal position and the clamp jaws pressed inboard, the angled portions of the distraction guide may be moved to a laterally inward position, thereby causing the ramps to be maximally distracted for a given position of the distraction guides with respect to the ramps along the longitudinal axis of the insertion instrument.

In one or more embodiments, when the tube member is in the distal position, and the distraction ramps are at their greatest height in relation to the implant, the ramps can be slid along the guides and moved into an advanced position in which the distal-end distraction tips of the ramp segments project beyond the implant and the distraction guide. In one or more embodiments, the distal-end distraction tips may be configured for facilitated slide-fit reception into the intervertebral space, and may include stops defining an insertion limit or depth guide. The implant carried by the clamp jaw components at the distal end of the inserter body may then be advanced, such as by impact advancement, ratchet advancement, and/or threaded screw like advancement, between the distraction ramps in a distal direction toward the intervertebral space. Such advancement of the implant may be accompanied by distraction or spreading of the distraction ramps by engagement with the distraction wedge, and by corresponding distraction of the intervertebral space. Implant advancement may continue until the implant is positioned within the intervertebral distraction space. In one or more embodiments, the combined height of the distraction ramps and guide may be greater than the thickness of the implant. One or more further embodiments of the distal portion of the implant insertion device may terminate in two flat metallic tabs oriented superiorly and anteriorly to the respective vertebral bodies which insert into the cavity and have for their purpose the distraction of vertebral bodies and further act to gently transfer the final compressive load to the implanted device. Therefore, the implant may experience little or no force during the insertion process.

In one or more embodiments, once the implant is suitably advanced into the distraction space between the adjacent spinal vertebrae, the ramps may be positioned such that the tang portion of the ramps may be adjacent to the implant, with no portion of the ramps being located between the implant and the vertebral bodies. However, at this stage, the compressive force from the vertebral bodies may still be supported by the ramps and the distraction guides. The tube member may then be retracted into a proximal position by suitably rotating the knob, thereby allowing the arm members to slide laterally outward, which may thereby release the implant from the clamp jaws. As the distraction guides move laterally outward along with the arm members, the angled faces of the ramps may slide down the angled surface of the outwardly moving distraction guides, thereby decreasing the combined height of the ramps until the vertebrae-contacting surfaces of the ramps are separated by a distance that is less than the thickness of the implant. This movement may gradually transfer the compressive force urging the adjacent vertebral bodies together from the ramp tips to the implant. In one or more embodiments, the transfer of the compressive load off the ramps may be operable to enable the ramps to be easily removed from the intervertebral cavity without disturbing the placement or positioning of the implant. Additionally, with the load removed from the distraction guide, and therefore the inserter, the inserter can also be easily removed.

One or more embodiments of an implant insertion instrument 10 for placement of an implant G into a space between adjacent bony structures such as between a pair of adjacent spinal vertebrae are described herein. The insertion instrument 10 may be used with any type of bone support implant G, such as a fusion device, or with alternative constructs including but not limited to spacer devices and/or artificial joint components.

Other features and advantages of the present invention will become more apparent from the following detailed description, taken in conjunction with the accompanying drawings which illustrate, by way of example, the principles of the invention.

BRIEF DESCRIPTION OF THE DRAWINGS

For the purposes of illustration, there are forms shown in the drawings that are presently preferred, it being understood, however, that the invention is not limited to the precise arrangements and instrumentalities shown.

FIG. 2 is a perspective view of the insertion instrument of FIG. 1 with the distraction ramps and implant removed;

FIG. 3 is a perspective view of a portion of the insertion instrument in FIG. 2, illustrating an implant carried by distraction guides including pair of clamp jaw components at a distal end of an elongated inserter body, in accordance with one or more embodiments of the present invention;

FIG. 8 is a side view of a portion of the insertion instrument of FIG. 7, in which the ramp units are in an advanced position, with the distal tips of the ramps inserted into an intervertebral cavity between adjacent vertebral bodies, in accordance with one or more embodiments of the present invention;

FIG. 9 is side view of a portion of the insertion instrument of FIG. 8 in which the distraction guides have been advanced toward the intervertebral cavity, thereby distracting the vertebral bodies, in accordance with one or more embodiments of the present invention;

FIG. 10 is a side view of a portion of the insertion instrument of FIG. 9 in which the distraction guides have been advanced to a final position in relation to the vertebral bodies and the distraction ramps, in accordance with one or more embodiments of the present invention;

FIG. 11 is a side view along the elongated midline of the insertion instrument of FIG. 8, illustrating the lesser height of the implant in relation to the combined height of the ramp tips and distraction guide, in accordance with one or more embodiments of the present invention;

FIG. 12 is a side elevational view of the insertion instrument depicting the retraction of a tube member with respect to the ramps and the resulting decrease in the combined height of the distraction ramps in accordance with one or more embodiments of the present invention;

FIG. 13 is a side view of the insertion instrument of FIG. 12 showing the engagement of an implant having a height that is greater than the combined height of the distraction ramps and distraction guides, in accordance with one or more embodiments of the invention;

FIG. 17 is an exploded perspective view of the insertion instrument of FIG. 16, in accordance with one or more embodiments of the present invention;

FIG. 18 is a perspective view of a portion of the insertion instrument and implant of FIG. 16, with the distraction ramp elements hidden to illustrate the clamp jaw mechanism and the implant, in accordance with one or more alternative embodiments of the present invention;

DETAILED DESCRIPTION OF THE PREFERRED EMBODIMENTS

Figure 1:
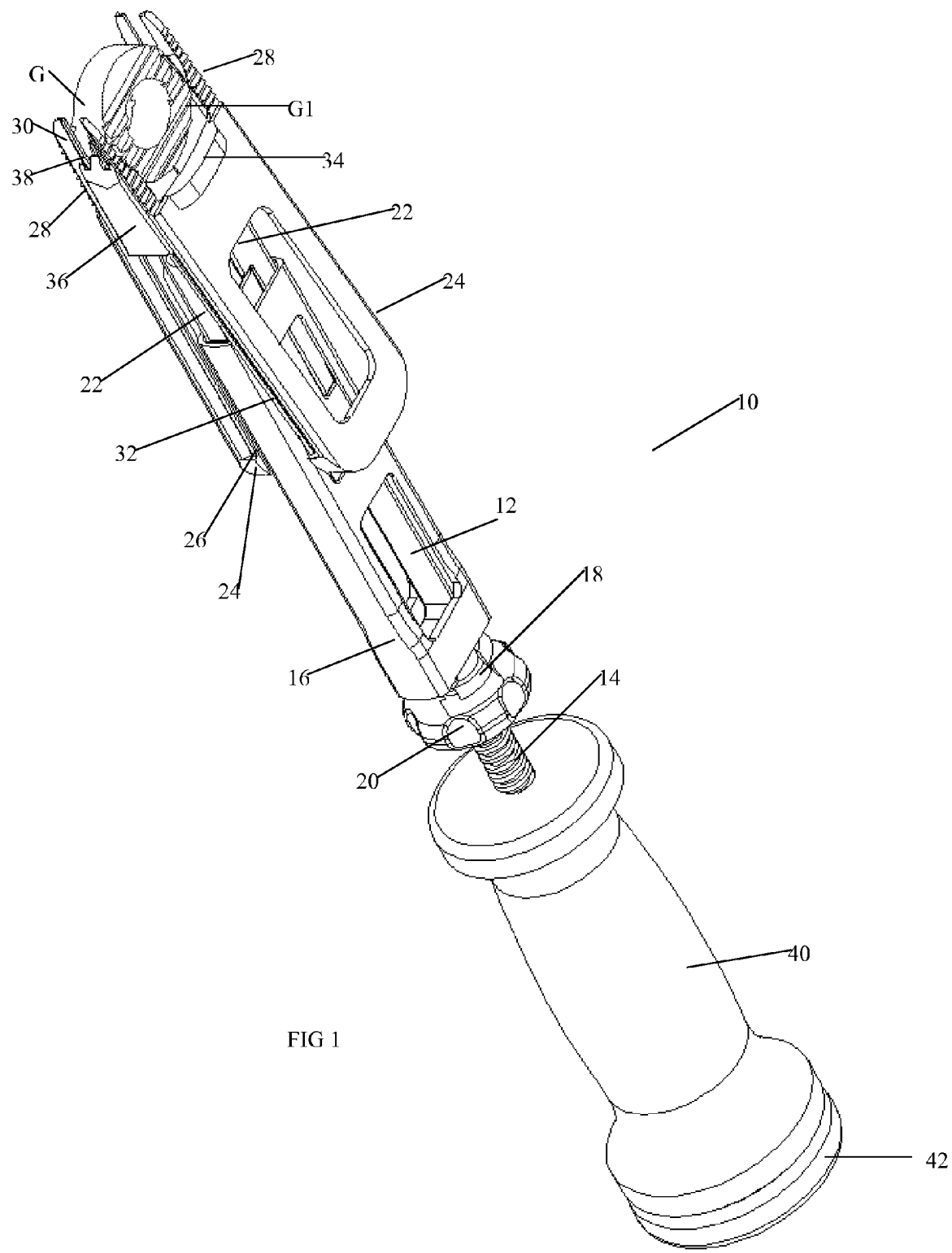
FIG. 1 is a right side perspective view of an intervertebral implant insertion instrument for use in distracting adjacent bony structures such as adjacent spinal vertebrae, and/or for inserting an implant and/or transplant of selected size and shape therebetween, in accordance with one or more embodiments of the present invention.
Figure 4:
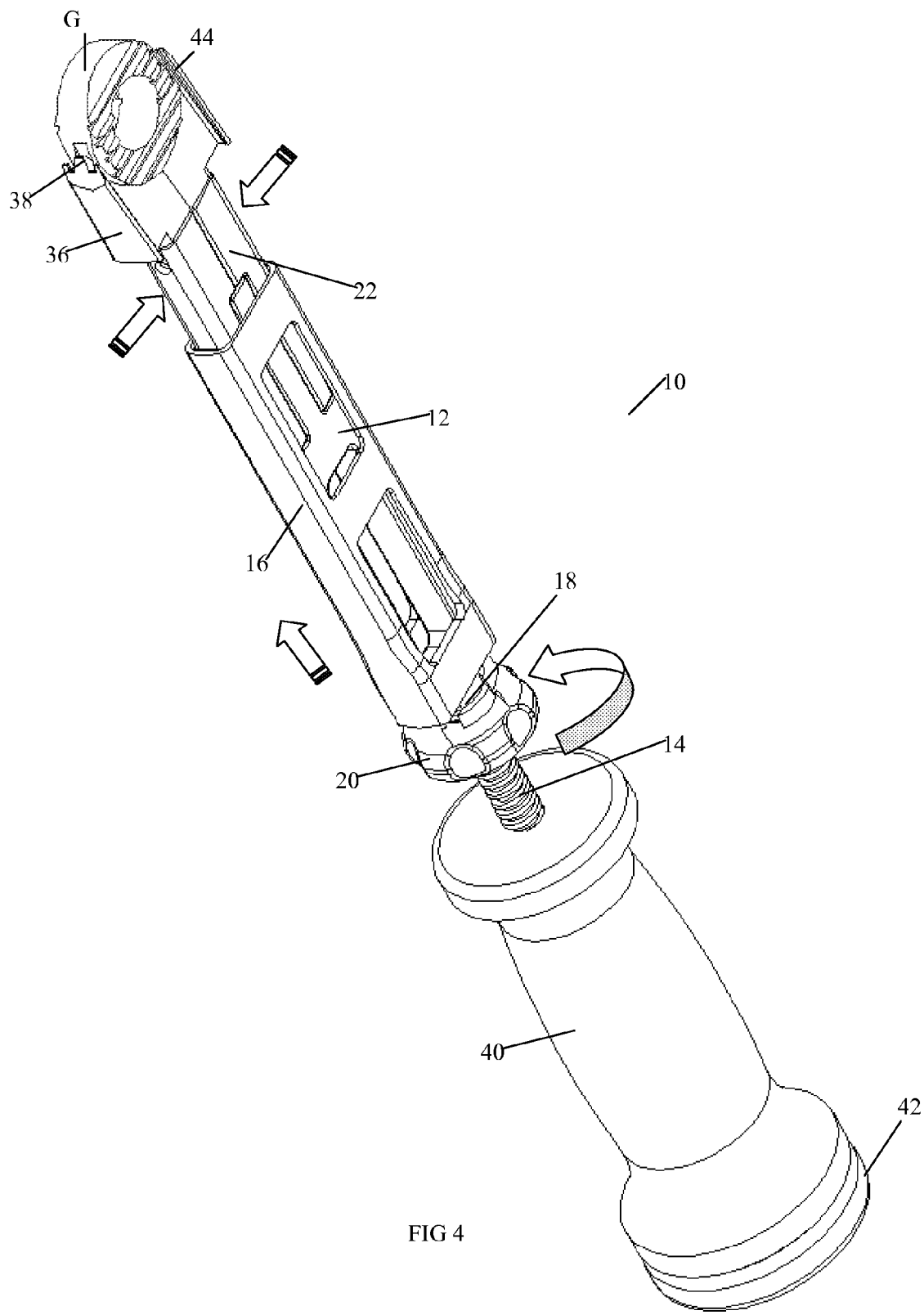
FIG. 4 is a perspective view of the insertion instrument of FIG. 2, depicting an implant being grasped by the clamp jaw components, in accordance with one or more embodiments of the present invention.
Figure 5:
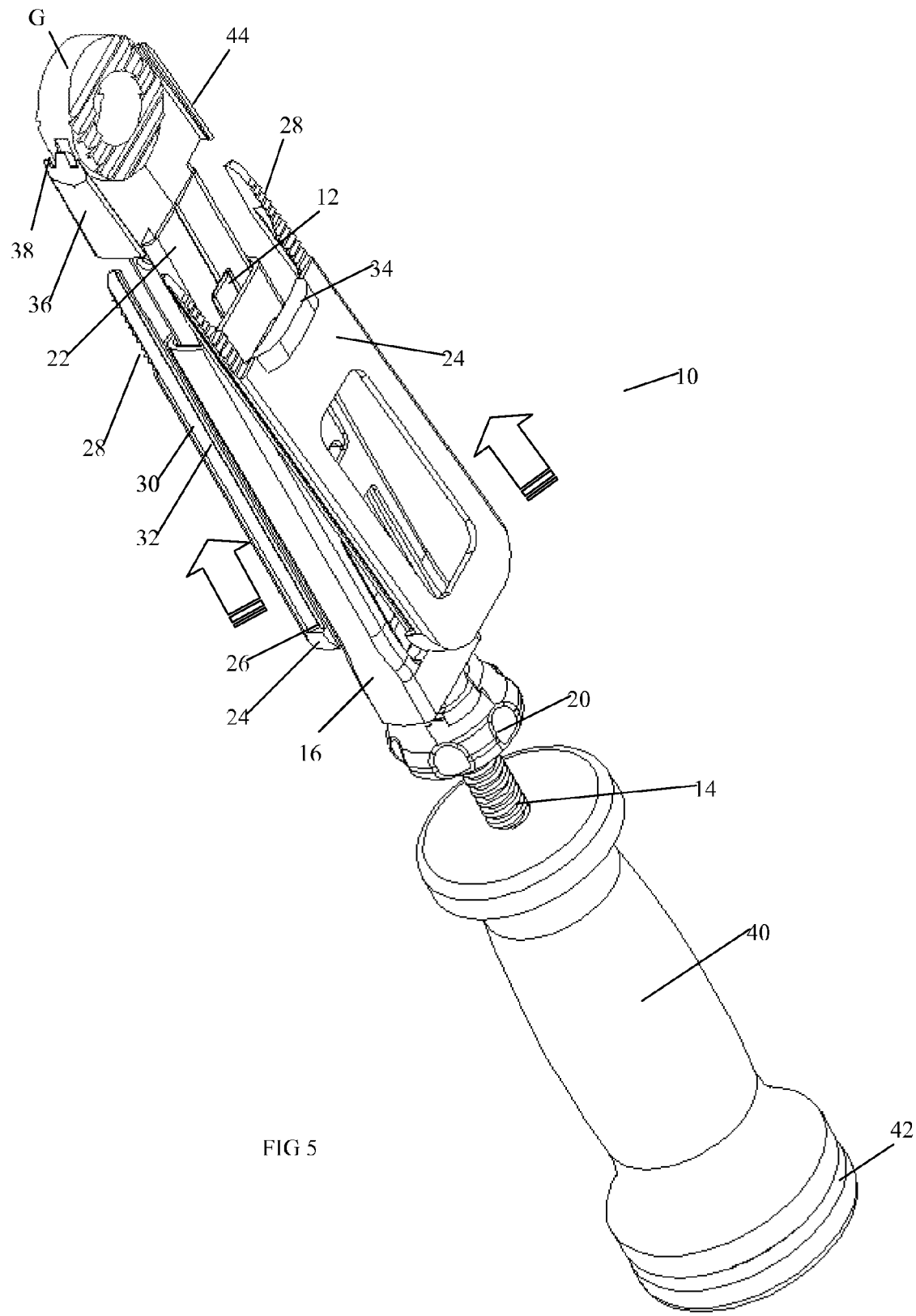
FIG. 5 is a perspective view of the insertion instrument of FIG. 4 showing the sliding removable mounting of the distraction ramps into the distraction guides, in accordance with one or more embodiments of the present invention.

FIG. 1 is a right side perspective view of an intervertebral implant insertion instrument 10 for use in distracting adjacent bony structures such as adjacent spinal vertebrae V1 and V2, and/or for inserting an implant G and/or transplant of selected size and shape therebetween, in accordance with one or more embodiments of the present invention.

In one or more embodiments, the insertion instrument 10 and related implant G may be adapted for use in spinal surgical procedures for placement of the implant G into a distracted intervertebral space wherein the implant G may subsequently serve as a load bearing spacer element for maintaining a prescribed spacing between adjacent vertebral structures (or "vertebrae") V1 and V2. In this regard, the implant G may be formed from a relatively sturdy and biocompatible material such as (but not limited to) a selected metal or metal alloy, bone, polymer, carbon fiber-reinforced polymer and/or ceramic. The implant G may be formed with a partially open or porous configuration and may be coated or partially filled with a selected bone ingrowth-enhancing substance, such as autogenous bone material harvested from the patient, with transplantable allogenic bone material supplied by a third party donor. Such devices, when implanted into the intervertebral space, may promote ingrowth of blood supply and live bone cells from the adjacent spinal vertebrae V1, V2 to inter-knit with the implant G, thereby eventually immobilizing or fusing the adjacent spinal vertebrae V1, V2.

In one or more embodiments, insertion instrument 10 may include handle 40 which may include impaction cap 42 at its proximal end, base component 12, tube component 16 which may include flange 18, and knob 20 which may include internal threads 62 (FIG. 15) and which may rotate about shaft 60 having threads 14. Base 12 may include slideable arms 22 which may have angled faces 48, which arms 22 may in turn move distraction guides 36. In one or more embodiments, insertion instrument 10 may further include distraction guides 36, which may in turn include angled faces 44, grooves 38, flat face(s) 50 for contacting an implant, and/or clamp components 46. In one or more embodiments, insertion instrument 10 may further include distraction ramps (or simply "ramps") 24, which may in turn include stopper (or "stop") 26, distraction faces 28, angled faces 30, flanges 32, and/or depth stops 34.

One or more embodiments of the present invention may be operable to insert an implant G into an interbody cavity while avoiding imparting any compressive force, or shear force, to the implant until the implant is located in its final position in an interbody cavity, which may be an intervertebral cavity. Moreover, one or more embodiments of the present invention may enable the insertion instrument 10 to be extracted from the interbody cavity without being subjected to compressive or shear forces from the adjacent bodies during such extraction. Avoidance of such compressive and/or shear forces may enable avoiding damage to the adjacent bodies and/or to the insertion instrument. Further, one or more embodiments of the present invention may be operable to maintain an initial angle between the ramps 24 of insertion instrument 10 during expansion of the interbody cavity, thereby enabling maintenance of a constant lordotic angle between the adjacent bodies being separated by insertion instrument 10. Further, once the implant G is in a final position between the adjacent bodies, one or more embodiments of the present invention may be operable to gradually transfer the compressive force, urging the adjacent bodies together, from the ramps 24 and distraction guides 36 to the implant, thereby avoiding any sudden undesirable impact forces upon either the implant G or the either or the adjacent bodies.

Insertion instrument 10 may include one or more ramps 24, which may slide with respect to a mating surface on distraction guides 36, and which may be configured for quickly and easily distracting, or separating, an interbody cavity between two adjacent bodies, or more particularly, an intervertebral cavity between two adjacent vertebral bodies. In one or more embodiments, insertion instrument 10 may operate to distract an intervertebral cavity (such as between V1 and V2 in FIG. 8) at a substantially optimized insertion and distraction angle for facilitated placement of the implant G having a height selected from a range of different heights according to individual patient requirements. Moreover, in one or more embodiments, insertion instrument 10 may protect the implant G against substantial compression and/or shear forces during intervertebral distraction and implant placement into the intervertebral cavity or "intervertebral space". In one or more embodiments, instrument 10 may include at least one removable distraction guide 36 which may include a pair of clamp components 46 for securely supporting and retaining the implant G during intervertebral placement. Insertion instrument 10 may further include a tube mechanism, or simply "tube", 16 which may be operationally coupled to the clamp components 46 for quickly and easily releasing the implant G within the intervertebral space.

FIGS. 1-5 and 15 depict stages of a method for setting up instrument 10 prior to insertion of the implant G in accordance with one or more embodiments of the present invention. A pair of distraction guides 36 may be removably mounted to a pair of slideable arms 22. Distraction guides 36 may be shaped and sized to correspond with the size and shape of a specific implant G which may be selected for a particular insertion operation. Distraction guides 36 may configured to match the size and shape of a wide range of possible implants G.

Figure 15:
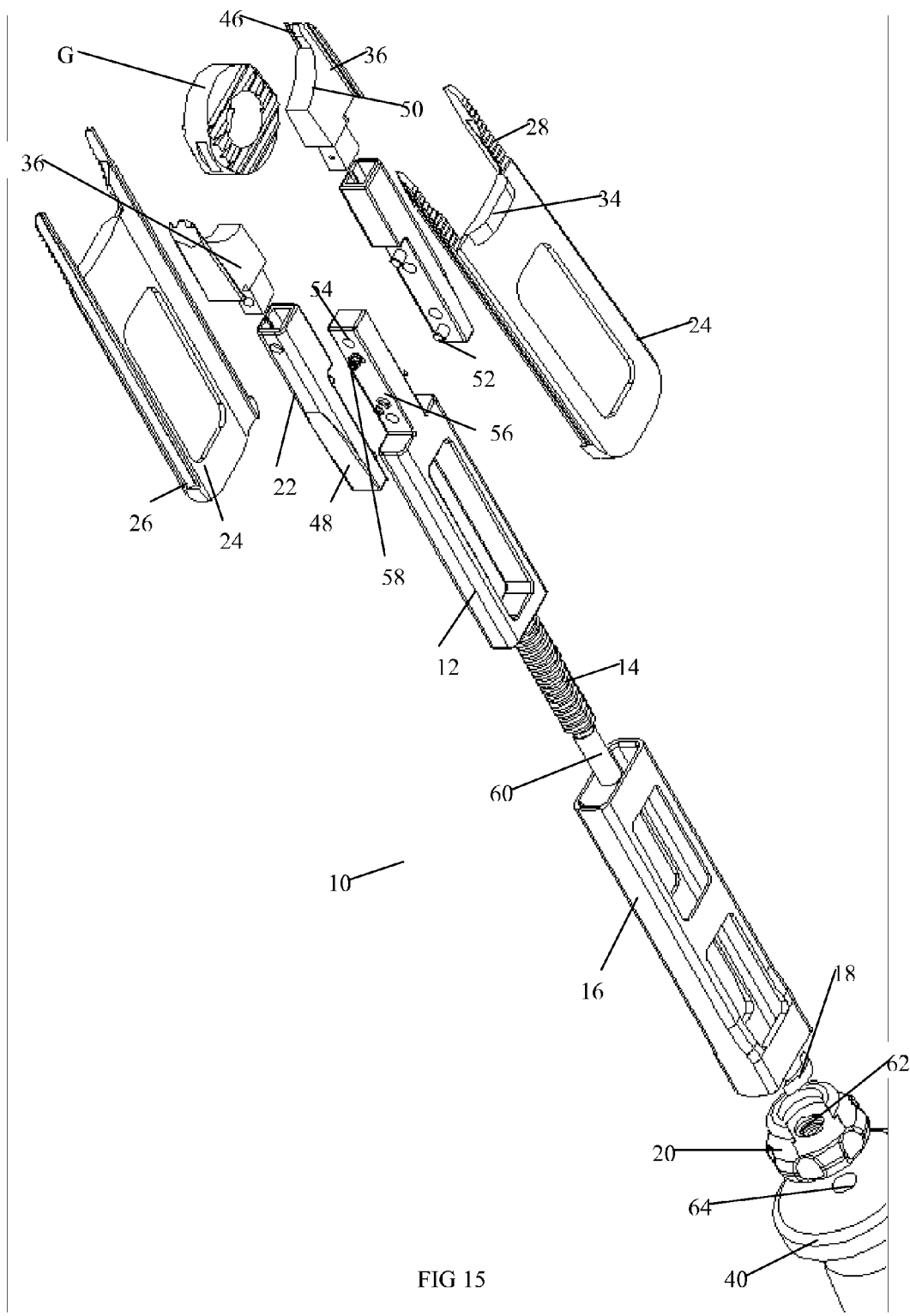
FIG. 15 is an exploded perspective view of the insertion instrument of FIG. 1 and an implant suitable for insertion therewith, in accordance with one or more embodiments of the present invention.

Directing attention to FIG. 15, a portion of base 12 of insertion instrument 10 may include guide pins 52 which may mate with holes 54 of slideable arms 22. Base 12 may further include holes 58 into which springs 56 may be mounted. Base 12 may further include post 60. Further, knob 20 may include internal threads 62 which may engage threads 14 of post 60, and handle 40 may include internal threads 64.

Still directing attention to FIG. 15, arms 22 may move laterally in relation to the base 12. Otherwise stated, arms 22 may move within a plane parallel to the plane of the serrated upper and lower surfaces of implant G in the view of FIG. 15. Arms 22 may move employing sliding contact with adjacent surfaces, or alternatively using a roller interface, or other suitable mechanism for movement of arms 22 with respect to surfaces remaining stationary within insertion instrument 10. Guide pins 52 on the laterally inward side of arms 22 may reside within holes 54 on the base 12 to enable the laterally directed motion of the arms 22. A pair of springs 56 (FIG. 15) may be positioned within a second set of lateral holes 58 in the base 12. This arrangement of springs 56 serve to force the arms 22, and thereby the distraction guides 36, out laterally in the absence of any opposing force.

Directing attention to FIG. 2, tube 16 may move with respect to base 12 along a longitudinal axis thereof to either open (expand)_or close (contract) arms 22. Motion of the tube 16 with respect to the base 12 may be effected by rotating threaded knob 20 in the desired direction. Knob 20 may have internal threads 62 that mate with threads 14 on shaft 60 on the body 12. Tube 16 may include a cylindrical flange 18 at the proximal end thereof, which may operate to maintain a constant linear distance between the knob 20 and the tube 16. Employing the apparatus described above, knob 20 may advance or retract the tube 16 into the desired position with respect to tube 12. As the tube 16 moves toward the implant G, the internal edges of the tube 16 may engage the angled faces 48 of the arms 22, thereby bringing the arms together and causing the distraction guides 36 to grasp the implant G. The knob 20 and the tube 16 may be prevented from retracting too far by threading the handle 40 onto the rear of the body 12 using internal threads 64 of the handle 40.

In one or more embodiments, distraction guides 36 may be removably attached to slideable arms 22. Thus, in such embodiments, as the arms 22 move laterally inward and outward with respect to the base 12, distraction guides 36 may track the movement of the arms 22. As the distraction guides 36 move inward, the clamps 46 of the distraction guides 36 may make contact with the lateral walls of the implant G to hold the implant G in place. Furthermore, the flat face 50 of the distraction guides 36 may press against a proximal wall portion (the portion facing toward instrument 10) of the implant G to ensure proper positioning of the implant. Once the implant G is securely grasped by the distraction guides 36, the ramps 24 can be slid into position. The medial face (inner face) of the guides 36 may include one or more grooves 38 and/or one or more angled faces 44. When viewing insertion instrument 10 from its distal end (FIG. 6), the angled faces 44 of the distraction guides 36 may form portions of V-shaped surfaces for engaging corresponding surfaces on ramps 24. In one or more embodiments, each distraction guide 36 may include one upper slanted surface 44 and one lower slanted surface 44 for engaging respective surfaces of ramps 24. The upper and lower faces 44 of distraction guides 36 may be oriented at a generally lordotic angle with respect to one another, which arrangement may cause the longitudinal axes of the upper and lower ramps 24 to also be oriented at this lordotic angle with respect to one another. Each of grooves 38 and faces 44 of the distraction guides 36 may extend along an axis corresponding to the proximal-distal axis of a corresponding ramp 24. The foregoing may apply to both the upper groove 38 and face 44 and the lower groove 38 and face 44 of each distraction guide 36.

Figure 7:
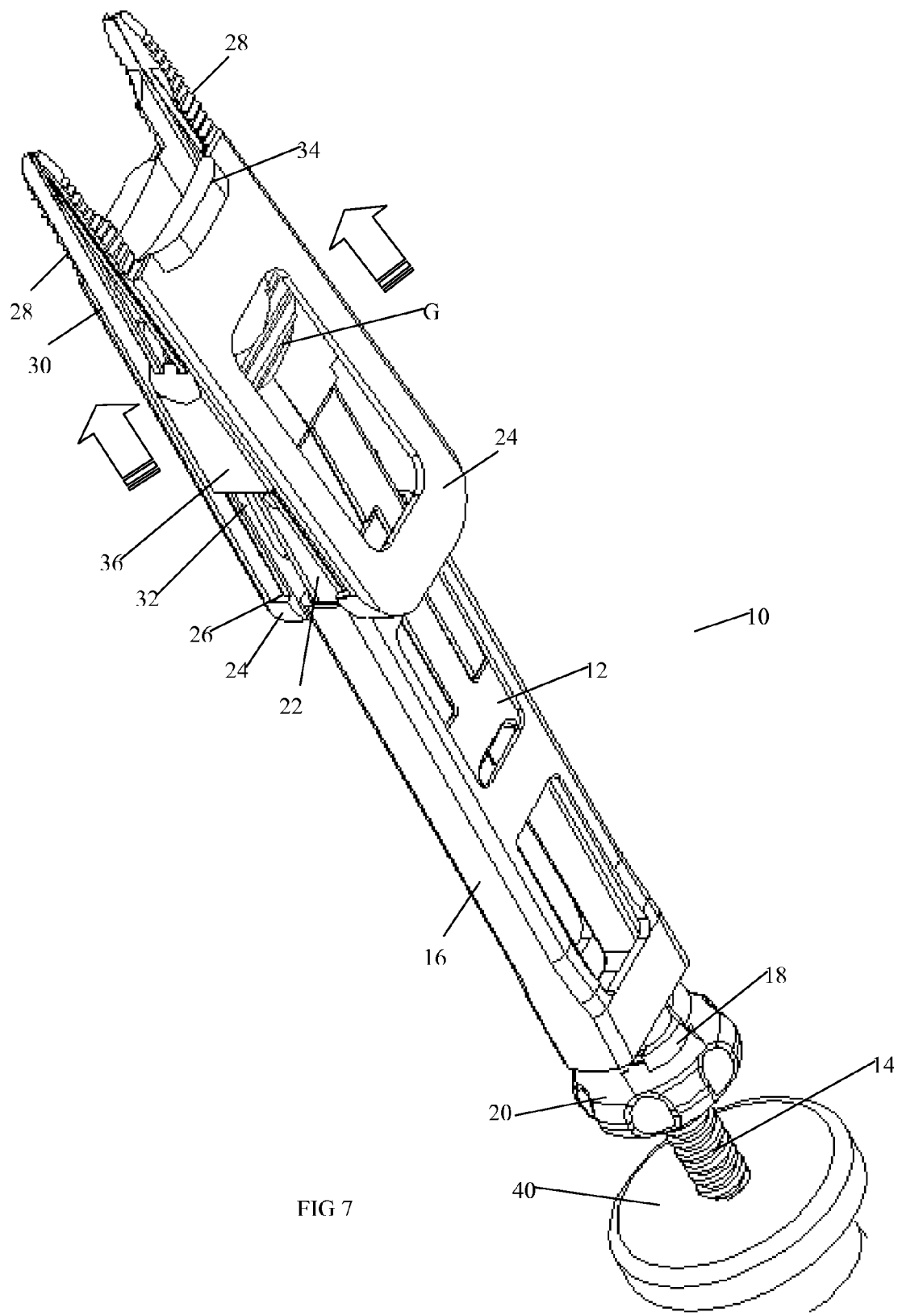
FIG. 7 is a perspective view of the distal end of the inserter of FIG. 4 showing the slideable, removable distraction ramps in an advanced position in relation to the distraction guides, in accordance with one or more embodiments of the present invention.

Each edge of each ramp 24 may include a flange 32 and angled face 30 corresponding to the groove 38 and face 44, respectively, of the distraction guide 36 with which the ramp 24 edge interfaces. The flange 32 of each ramp 24 and the groove 38 of the corresponding distraction guide 36 may slide with respect to one another as the ramps 24 move with respect to the distraction guides 36. The angled faces 30 of the ramps 24 may be shaped so as to form a portion of a V-shaped surface with the point of the "V" pointed towards the implant G. The ramps 24 may be slid forward until the stops 26 of the ramps 24 make contact with respective rear portions (portions facing the proximal end of the instrument 10) of the guides 36, as shown in FIG. 7. Advancing the ramps 24 with respect to the distraction guides 36 in this manner may operate to present a thinner profile for instrument 10, and a more acute angle between (the longitudinal axes of) the ramps 24. This more acute angle between ramps 24 may enable the insertion instrument 10 to more effectively advance into a space between adjacent bodies, such as adjacent vertebrae, and to create an initial interbody cavity prior to expanding this interbody cavity via movement of the distraction guides with respect to the ramps 24.

Figure 6:
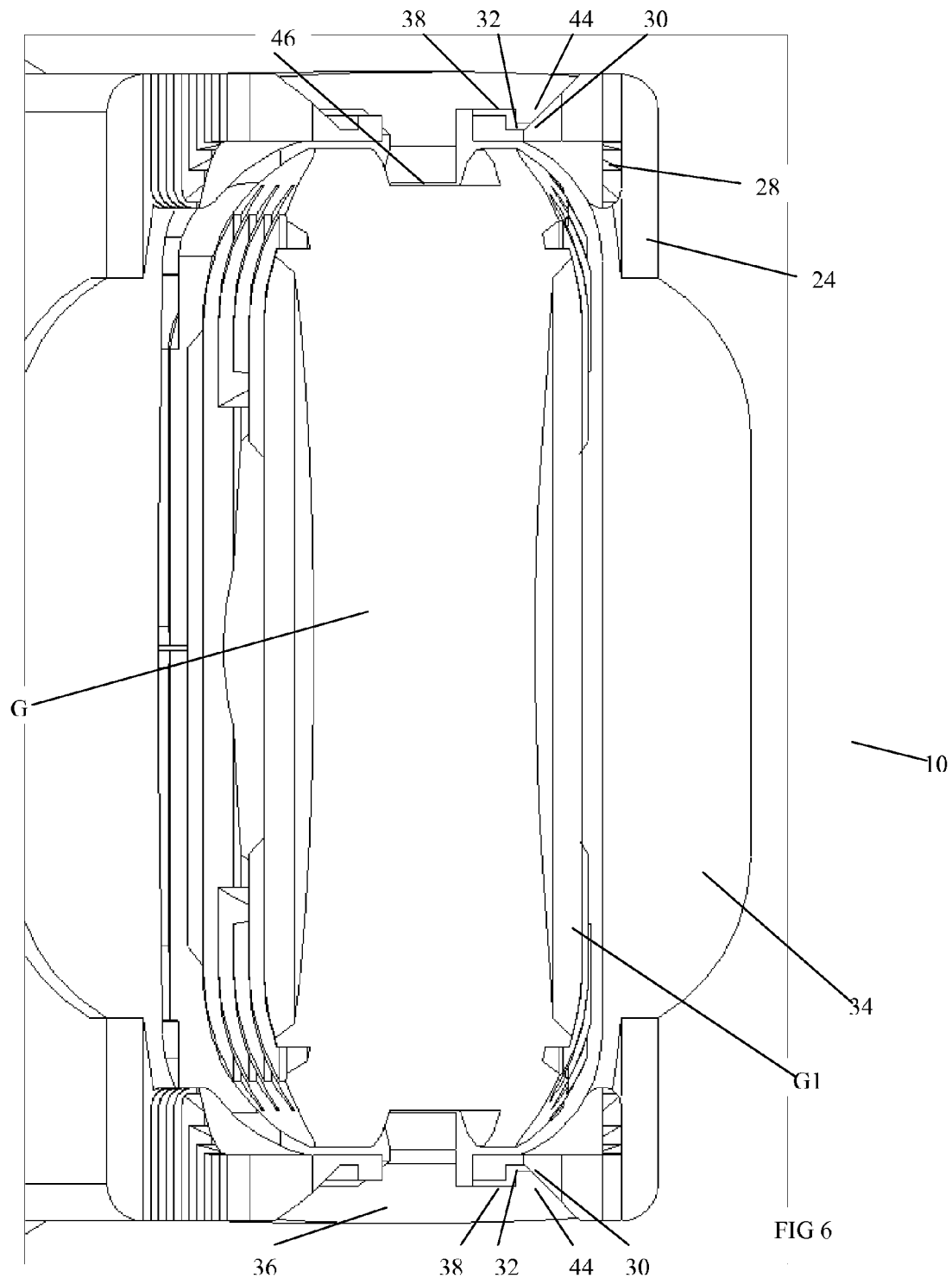
FIG. 6 is an elevational view of the front of the insertion instrument of FIG. 5, in accordance with one or more embodiments of the invention.

FIG. 6 depicts the interaction between the implant G, the distraction guides 36, and the ramps 24, in accordance with one or more embodiments of the present invention. As the flanges 32 of ramps 24 engage the grooves 38 of guides 36, the angled faces 44 of the guides 36 and angled faces 30 of the ramps 24 may contact one another. More specifically, the ramps 24 may move atop (in the case of the upper ramp 24) the angled face 44 of the distraction guides 36. In FIG. 6, the distraction guides 36 are in the medial (inward) position, and may thereby operate to grasp the implant G. The guides 36 may operate to resist any compressive force operating to urge the ramps 24 together and to thereby avoid loading implant G with any of the compressive force. It is noted that the overall height of the ramps 24 may be determined by the position of the distraction guides 36 with respect to the ramps 24 along the lateral axis of the body 12 (the axis from left to right in the view of FIG. 6).

In one or more embodiments, the ramps 24 may include distraction faces 28 on the outer surfaces thereof (the surfaces 28 being configured to contact the adjacent bodies such as vertebral bodies). The distraction faces 28 may have surfaces that are roughened in some manner, with one or more of serrations, knurling, chemical etching, and/or other surface modifications. In one or more embodiments, when the distraction guides 36 are in the fully inward position, the distance between the distraction faces 28 of the ramps 24 may be greater than the thickness of the implant G, which may enable the ramps 24 and the guides 36 to receive the entirety of the compressive force urging adjacent bodies together, thereby shielding the implant from this compressive force during the implant insertion process. At the same time, the thickness of the implant G may be less than the distance between the inner surfaces of the ramps 24, thereby allowing the ramps to slide over the implant without contacting it.

FIGS. 8-14 depict various stages of insertion of the implant G between a pair of vertebral bodies V1 and V2 by the insertion instrument 10, in accordance with one or more embodiments of the present invention. With reference to FIG. 8, the ramps 24 are in the most extended position with respect to the distraction guides 36 along the longitudinal axis of insertion instrument 10. Additionally, at this stage of the implant insertion process, the distraction guides 36 may be in the medial (inward) position as shown in FIG. 6. The distraction guides 36 may be maintained in this medial (inward) position by placing the tube 16 in its most forward or distal position with respect to the body 12. In one or more embodiments, when the distraction guides 36 are in the medial or inward position, the combined height of the ramps 24 may only slightly exceed that of the implant G. With this configuration of insertion instrument 10, the insertion instrument 10 may be advanced toward a surgical site leading with the ramps 24. The distal tips of the ramps 24 may be inserted into an intervertebral cavity between a pair of vertebral bodies V1 and V2 until the depth stops 34 contact the anterior surfaces (the surface facing toward the proximal end of insertion instrument 10) of the vertebral bodies V1 and V2. The entry of the ramps 24 into the intervertebral cavity may be facilitated by maintaining a lordotic angle between the ramps 24 using the distraction guides 36. During the insertion of insertion instrument 10 into the intervertebral cavity, ramps 24 may be prevented from undesirably retracting from the intervertebral cavity by virtue of the presence of frictional forces between distraction faces 28 on the tips of the ramps 24 and the surfaces of the adjacent vertebrae contacting surfaces 28. The body 12 of the device 10 may be advanced toward the vertebral bodies V1 and V2 by impacting the impaction cap 42, which may be located at the proximal end of the handle 40.

Having advanced the insertion instrument as a whole toward, and then into, the intervertebral cavity, it remains to distract, or expand, the cavity. As discussed below, this distraction may be accomplished by moving the distraction guides 36 distally along the longitudinal axis of insertion instrument 10, with respect to the ramps 24 to separate the ramps 24. As the instrument 10 advances, the distraction guides 36 may advance therewith. The grooves 38 on the medial (inward) side of the distraction guides 36 may slide along the flanges 32 of the ramps 24. Furthermore, because the angled faces 30 of the ramps 24 may rest on respective angled faces 44 of the distraction guides 36, the compressive force urging the adjacent vertebral bodies together (which may also be referred to herein as the "load") may be transferred through the ramps 24 to the distraction guides 36. The above-described approach, which enables the distraction guides 36 to receive all or at least substantially all of the compressive force urging the adjacent bodies together, may enable the system and method of the present invention to avoid loading the implant with any of the compressive force from the interbody cavity during the insertion of the implant into the interbody cavity. The advancement of the distraction guides 36 with respect to the ramps 24 distally along the longitudinal axis of the instrument 10 may operate to separate the ramps 24 while maintaining the angle between the ramps constant. Preferably, the angle between the ramps 24 that is being held constant is the lordotic angle suitable for the particular insertion process being conducted. In one or more embodiments, the preservation of the angle between the ramps 24 during the insertion process may cause the lordotic angle between the surfaces of the bodies V1 and V2 contacted by the ramps 24 to also remain constant throughout the implant insertion process. The above-described approach may provide parallel distraction of bodies V1 and V2 while preserving the desired lordotic angle between the bodies V1 and V2. This approach contrasts with existing approaches in which ramps or levers pivot about a common fulcrum, or about separate fulcrums, in which the angle between the surfaces of the intervertebral cavity is not maintained constant throughout the implant insertion process.

FIGS. 10 and 11 show the instrument 10 in the fully distracted position with the distraction guides 36 and implant G fully advanced into the intervertebral cavity, in accordance with one or more embodiments of the invention. At the insertion stage shown in FIGS. 10 and 11, the ramps 24 may be fully distracted. Still with reference to FIGS. 10 and 11, the implant G may be located in a desired final location between the adjacent vertebral bodies. The distance between the respective distraction faces 28 of the two ramps 24 may be slightly greater than the height of the implant G, thereby enabling the serrated faces G1 and G2 of the implant G to be free from contact with the vertebral bodies V1 and V2. Thus, at this stage of the insertion process, implant G may still be free of compressive force from the intervertebral bodies V1 and V2.

Figure 14:
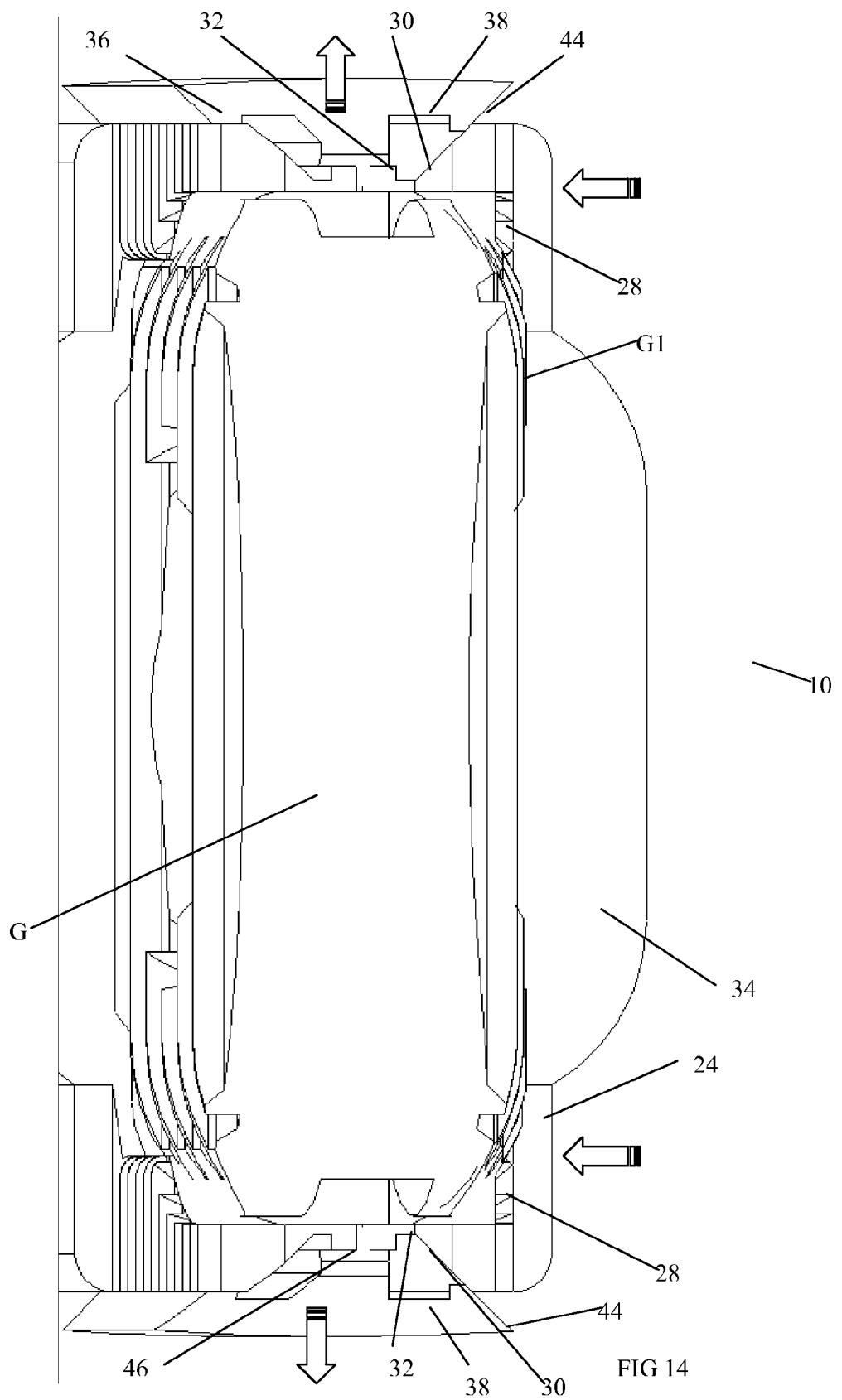
FIG. 14 is an elevational view of the insertion instrument of FIG. 13 from a vantage point at the left side of the view of FIG. 13 that shows the distraction guide, implant and clamp jaw components, wherein the guide and jaw components are in an laterally outward position and wherein the distance between the upper and lower outer surfaces of the distraction ramps is less than the thickness of the implant, in accordance with one or more embodiments of the present invention.

FIG. 12-14 demonstrate the final positioning of the implant G and the release of the implant G by the instrument 10, in accordance with one or more embodiments of the present invention. With the implant G in the desired position along the proximal-distal axis of the instrument 10 (the axis from left to right in FIGS. 10-11) in relation to the vertebral bodies V1 and V2, the tube component 16 may be retracted with respect to the body 12 of instrument 10 toward the proximal end of instrument 10. The retraction of tube 12 may be accomplished by rotating the knob 20 which may cause the tube 16 to move linearly toward the proximal end of instrument 10 and away from the vertebrae V (where "V" refers to the V1 and V2 together). As the tube 16 is retracted, the internal springs 56 (see FIG. 15) may cause the arms 22 to move out laterally away from a longitudinal center of instrument 10, which in turn may cause the distraction guides 36 to move out laterally as well. The lateral motion of the distraction guides 36 away from the center of instrument 10 may cause distraction guides to stop receiving, or otherwise stated, to stop resisting the compressive force imparted by the adjacent bodies V1 and V2. Thus, as the distraction guides 36 move out laterally, the compressive force from the adjacent bodies, which may no longer be opposed by the distraction guides, 36 may cause the ramps 24 to move toward each other, thereby enabling the vertebral bodies V1 and V2 to do the same.

Because the angled faces 30 of the ramps 24 may rest upon the corresponding angled faces 44 of the distraction guides 36, the ramps 24 may comply with the unopposed compressive force from the adjacent bodies and approach one another by moving into the expanding space between the laterally displaced distraction guides 36. The approach of the ramps towards one another may continue until the distance between the outer ramp 24 surfaces 28 is less than the thickness (or "height") of the implant G. As the distraction distance of the vertebral bodies V1 and V2 diminishes, the compressive force urging the adjacent bodies V1 and V2 together may be gradually transferred from the ramps 24 to the implant G. In one or more embodiments, the serrated faces G1 and G2 of the implant G may engage, or bite into, the endplates (implant-facing surfaces) of the corresponding vertebral bodies V1 and V2, as the upper and lower bodies V1 and V2 are urged together toward the upper and lower surfaces, respectively, of the implant G.

The above-discussed approach may enable the gradual transfer of the compressive force from the ramps 24 to the implant G and may enable the implant G to be securely held in place during the release of the implant by the instrument 10 and during the extraction of the instrument 10 from the intervertebral cavity. The above-discussed approach may also enable the instrument 10 to be extracted from the intervertebral cavity without the application of a compressive force thereon. Freeing the instrument from the compressive force in this manner, may help avoid damage to the instrument and/or to the implant during the instrument extraction. The ability to extract the instrument 10 from the interbody cavity while free of the application of compressive force from bodies V1 and V2 may be enabled by the shape of one or more embodiments of the distal portions of ramps 24, as best seen in FIG. 1. In the view of FIG. 1, it may be seen that the tangs or "finger portions" of the upper ramp 24 clear the edges of the implant along the plane of the upper surface of the implant. With this arrangement, as the ramps 24 close in on one another in response to the compressive force and the gradual removal of distraction guides 36, the ramp 24 tangs may move vertically along the sides of the implant G instead of coming to rest on the upper and lower surfaces of the implant G. In this manner, the ramp 24 tangs may avoid getting caught between the vertebral bodies and the implant G, as the vertebral bodies come to rest.

It is noted that existing systems and methods commonly include extracting levers of an instrument from an interbody cavity while a compressive force is still being applied thereto. Such existing approaches run the risk damaging the instrument during the extraction and/or of damaging the implant by suddenly shifting the compressive force from a lip or edge at the distal end of the insertion instrument to the implant itself as the lip or edge of the instrument clears the proximal edge of the adjacent intervertebral bodies.

Figure 16:
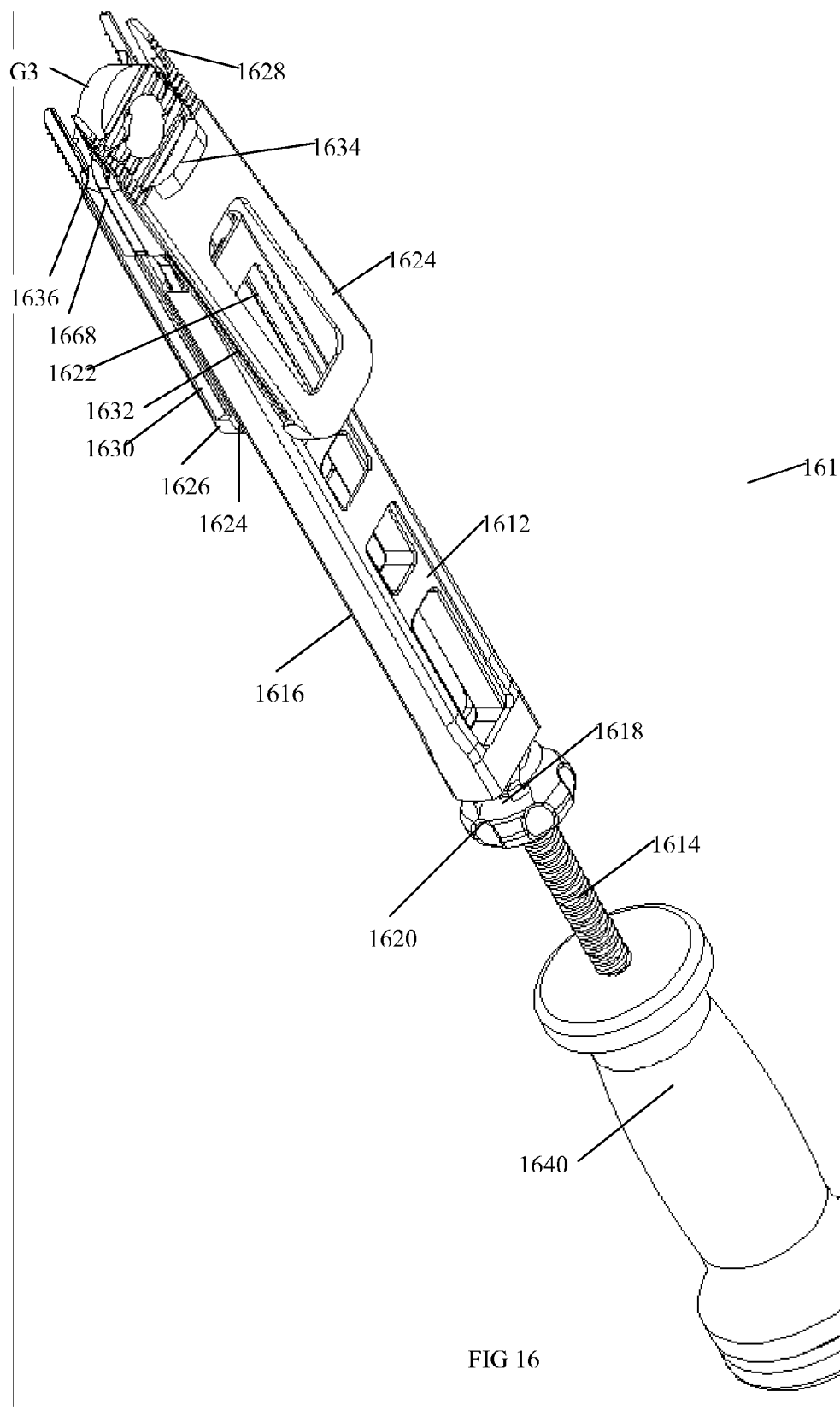
FIG. 16 is a perspective view of an implant insertion instrument for use in distracting adjacent bony structures such as adjacent spinal vertebrae, and for inserting an implant and/or transplant of selected size and shape therebetween, in accordance with one or more alternative embodiments of the present invention.

FIGS. 16-18 depict a method for setting up an instrument 1610 prior to insertion of the implant G3 in accordance with one or more alternative embodiments of the present invention. In one or more embodiments, a pair of distraction guides 1636 may be removably mounted to a pair of slideable arms 1622. The distraction guides 1636 may be shaped and sized to correspond with the size and shape of a particular implant G3 which has been chosen by a surgeon to conform to an individual patient's anatomy. Various embodiments of the distraction guides 1636 may be available to match various respective implants G3. The slideable arms 1622 may move laterally inward or outward in relation to the base 1612, as discussed in connection with the embodiments of FIGS. 1-15. With reference to FIG. 17, in one or more embodiments, guide pins 1652 on the medial (inward) side of the arms 1622 may be located within holes 1654 on the base 1612 to enable the lateral motion of the arms 1622. A pair of springs 1656 may be positioned within a second set of lateral holes 1658 in the base 1612. Springs 1656 may operate to force the arms 1622, and thereby the distraction guides 1636, laterally outward from base 1612.

Tube 1616 may move along base 1612 employing sliding contact, rolling contact, or other suitable motion interface. The motion of the tube 1616 may be controlled by rotating threaded knob 1620, as discussed in connection with other embodiments herein. The knob 1620 may include internal threads 1662 that mate with external threads 1614 located on a shaft 1660 extending from the base (or "body") 1612. A cylindrical flange 1618 at the proximal end of the tube 1616, may be operable to maintain a constant linear distance between the knob 1620 and the tube 1616. In one or more embodiments, the above described arrangement may enable rotation of the knob 1620 to move the tube 1616 to a desired position with respect to the body 12. Distal movement of the tube 1616 may be operable to force the slideable arms 1622 toward a laterally inward position. In one or more embodiments, as the tube 1616 moves distally along the instrument 1610, that is toward the implant G3, the inside edges of the tube 1616 may engage the angled faces 1648 of the arms 1622, thereby pushing the arms 1622 into a laterally inward position. The knob 1620 and the tube 1616 may be prevented from retracting too far with respect to the body 1612 by causing the internal threads 1664 of handle 1640 to engage the external threads 1614 of the body 1612.

Since the distraction guides 1636 may be removably attached to the slideable arms 1622, distraction guides 1636 may move laterally along with arms 1622. In one or more alternative embodiments, in addition to the movable distraction guides 1636, a pair of grasping jaws 1668 may be provided which may move within a cutout 1672 of the guides 1636. Grasping jaws 1668 may also have an angled face 1670 which is engaged by the tube 1616, as the tube 1616 advances distally with respect to the base 1612. As the jaws 1668 move laterally inward, the inner walls 1646 of jaws 1668 may press against the grooves G4 of the implant G3 to securely grasp the implant and to hold the implant in place. Furthermore, the flat faces 1650 of the guides 1636 may press against the proximal wall (the wall of the implant facing the proximal end of the instrument 1610) of the implant G3 to ensure proper positioning of the implant. While the implant G3 is securely grasped by the jaws 1668, the distraction guides 1636 may also be moved laterally inward by the tube component 1616, and the ramps 1624 can be slid into position. By incorporating the independent grasping jaws 1668 in one or more embodiments, the implant G3, which may have larger tolerances than the instrument 1610, may be securely grasped with greater reliability. Upon grasping the implant as described above, the instrument 1610 may conduct the implant G3 insertion operation and subsequent extraction of the insertion instrument 1610 in much the same manner as described in connection with FIGS. 8-14.

Figure 19:
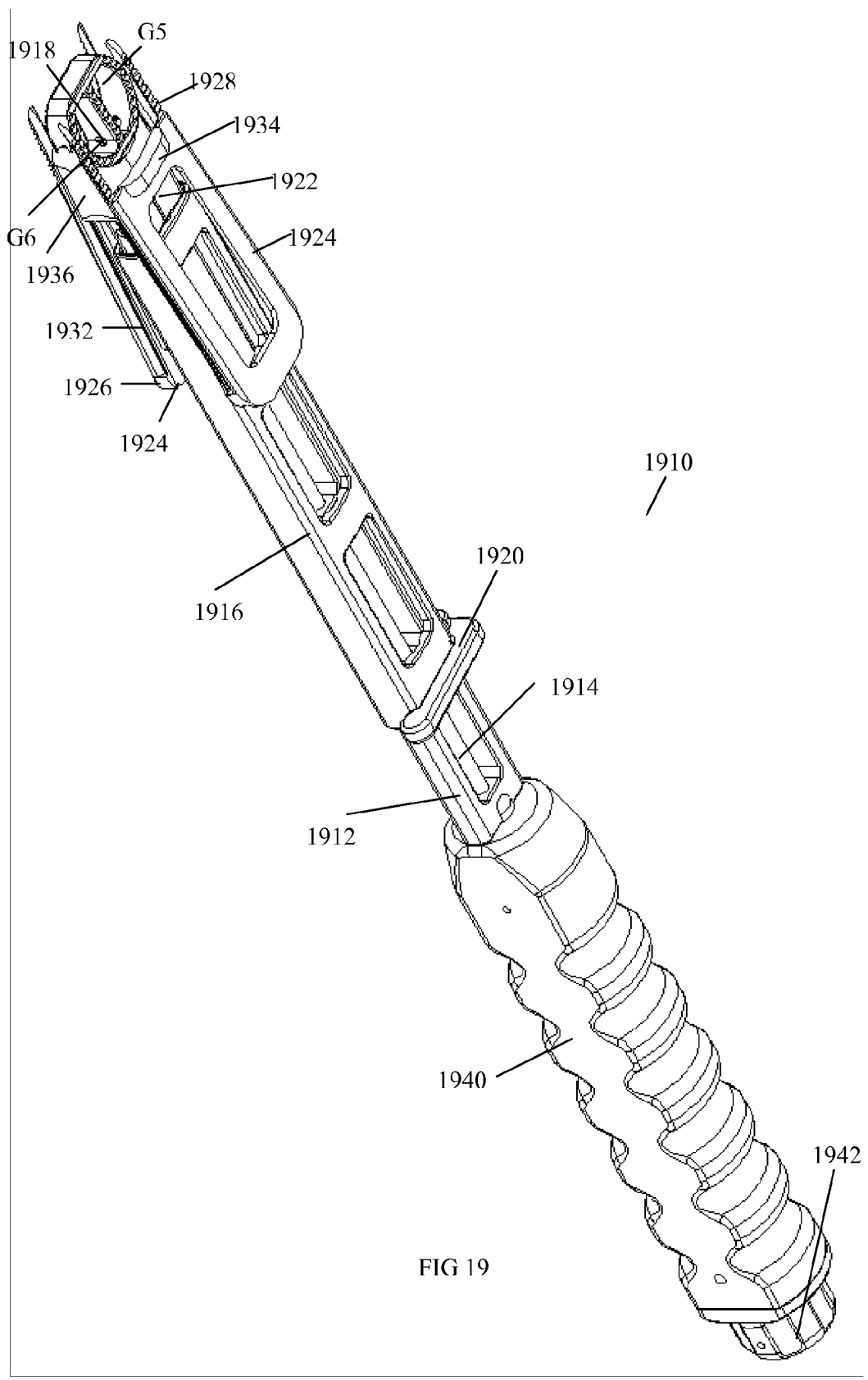
FIG. 19 is a perspective view of an implant insertion instrument for use in distracting adjacent bony structures such as adjacent spinal vertebrae, and for inserting an implant and/or transplant of selected size and shape there between, in accordance with one or more alternative embodiments of the present invention.
Figure 20:
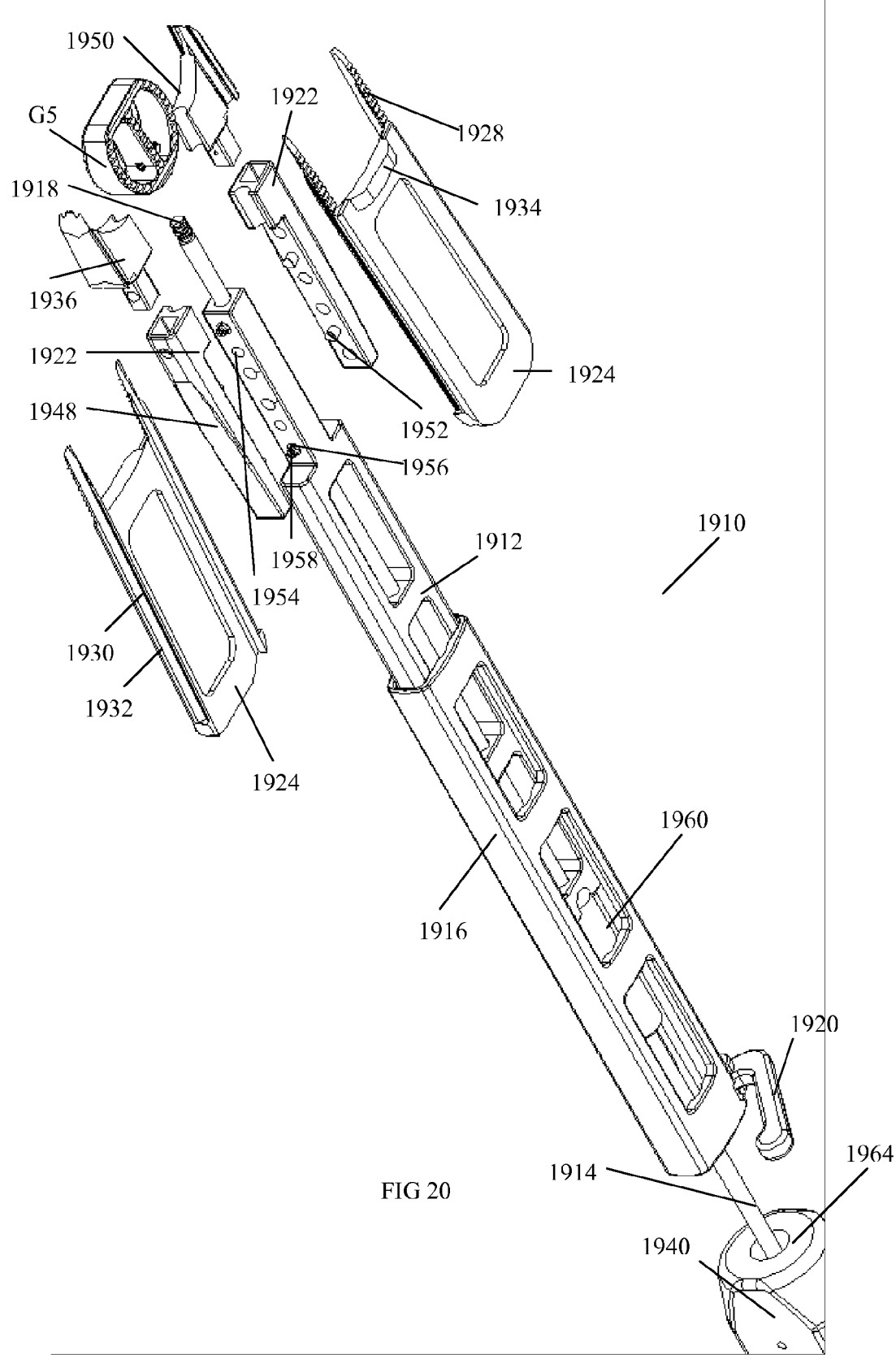
FIG. 20 is an exploded perspective view of the insertion instrument and implant of FIG. 19.
Figure 21:
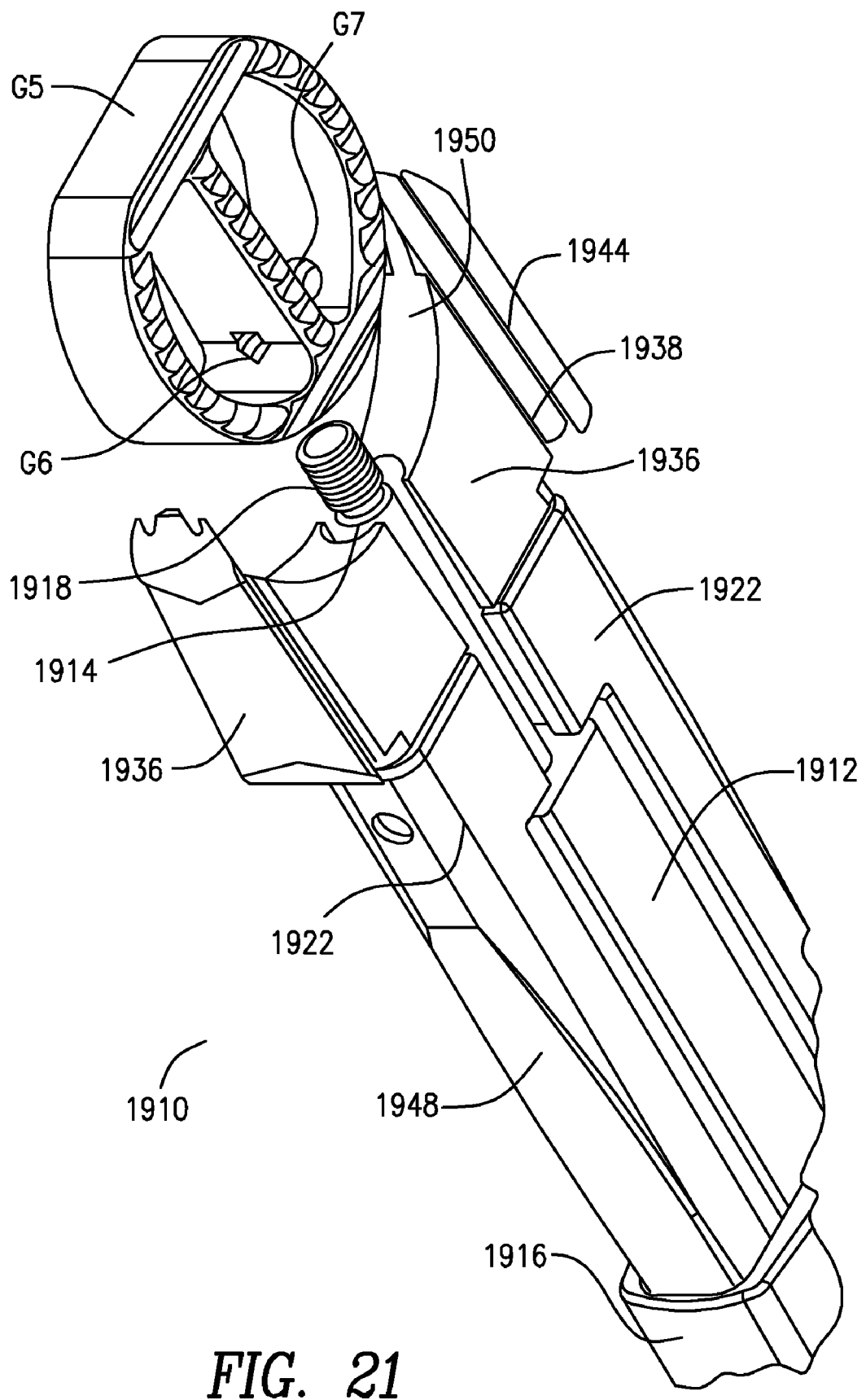
FIG. 21 is a close-up perspective view of a portion of the insertion instrument and implant of FIG. 19, with the distraction ramp elements hidden to illustrate the threaded engagement mechanism and the implant, in accordance with one or more embodiments of the present invention.
Figure 22:
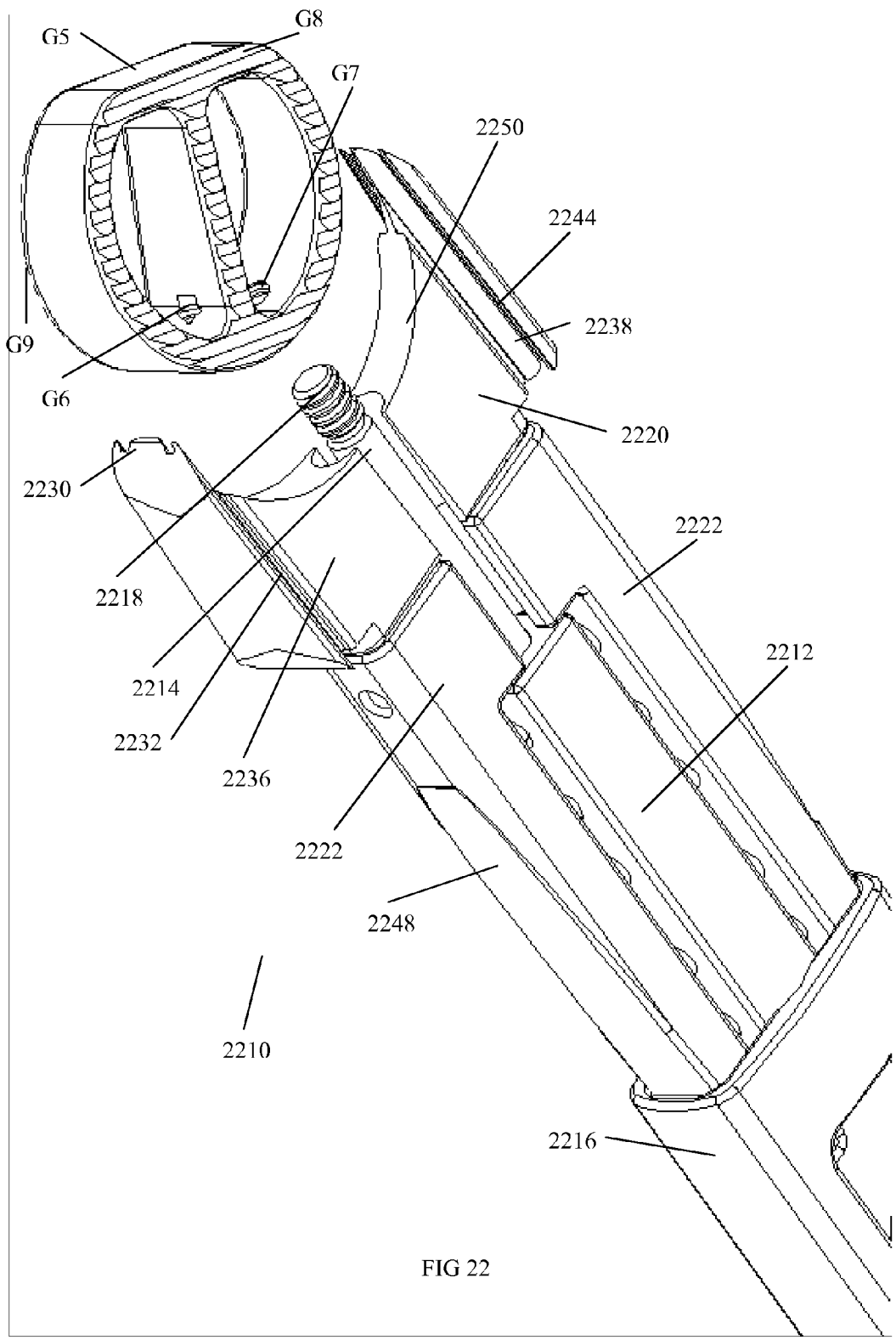
FIG. 22 is a perspective view of an implant insertion instrument for use in distracting adjacent bony structures such as adjacent spinal vertebrae, and for inserting an implant and/or transplant of selected size and shape therebetween, with the distraction ramp elements hidden to demonstrate the threaded engagement mechanism and the implant, in accordance with one or more alternative embodiments of the present invention.

FIGS. 19-21 depict a method for setting up yet another embodiment of an insertion instrument, instrument 1910, prior to insertion of an implant G5 into an interbody cavity, in accordance with one or more embodiments of the present invention. In one or more embodiments, a pair of distraction guides 1936 may be removably mounted to a pair of slideable arms 1922. The distraction guides 1936 may be shaped and sized to accommodate the size and shape of a particular implant G5 which has been chosen by a surgeon to suit a particular patient's anatomy. A plurality of distraction guides 1936 may have dimensions that are customized to match various respective implants G5. The slideable arms 1922 may move laterally inward and outward in relation to the base 1912. In one or more embodiments, guide pins 1952 on the medial side of the arms 1922 may be located within holes 1954 on the base 1912 to enable the lateral motion of the arms 1922. A pair of springs 1956 may be positioned within a second set of lateral holes 1958 in the base 1912. Springs 1956 may operate to force the arms 1922, and thereby the distraction guides 1936, laterally outward from base 1912.

Tube 1916 may move along base 1912 employing sliding contact, rolling contact, or other suitable motion interface. In one or more alternative embodiments, once the tube 1916 is in a desired position with respect to the base 1912, the tube 1916 may be locked into place using a locking arm 1920. The locking arm 1920 may create a friction lock between the base 1912 and the tube 1916. Movement of the tube 1916 may be operable to force the slideable arms 1922 toward a laterally inward position. In one or more embodiments, as the tube 1916 moves distally along the instrument 1910, that is toward the implant G5, the inside edges of the tube 1916 may engage the angled faces 1948 of the arms 1922, thereby pushing the arms 1922 into a laterally inward position. The tube 1916 may be prevented from retracting too far with respect to the body 1912 by inserting the small post 1960 that protrudes from body 1912 into the internal bore 1964 of handle 1940.

The implant G5 may be attached to the inserter 1910 by means of an elongated shaft 1914. The shaft 1914 may extend through the entire body 1912 and handle 1940 of the instrument 1910. The shaft 1914 may include a threaded tip 1918, at the distal end thereof, that may engage the implant G5 by means of a threaded hole G6 on the proximal side of the implant. The shaft 1914 may be rotated by a knob 1942 at the proximal end of the shaft 1914. Since the distraction guides 1936 may be removably attached to the slideable arms 1922, as the arms 1922 move laterally inward and outward, the distraction guides 1936 may move along with the arms 1922. As the distraction guides 1936 move laterally inward, the inner faces 1950 of guides 1936 may press against the perimeter of the implant G5 and may thereby hold the implant in place. Once the implant G5 is securely held by the threaded shaft 1914, the ramps 1924 can be slid into position. The processes of a) assembling the ramps 1924 to the instrument 1910 and b) the subsequent insertion of the implant G5 within an intervertebral cavity are similar to what was discussed in connection with FIGS. 5-14. Accordingly, that discussion is not repeated in this section.

Figure 23:
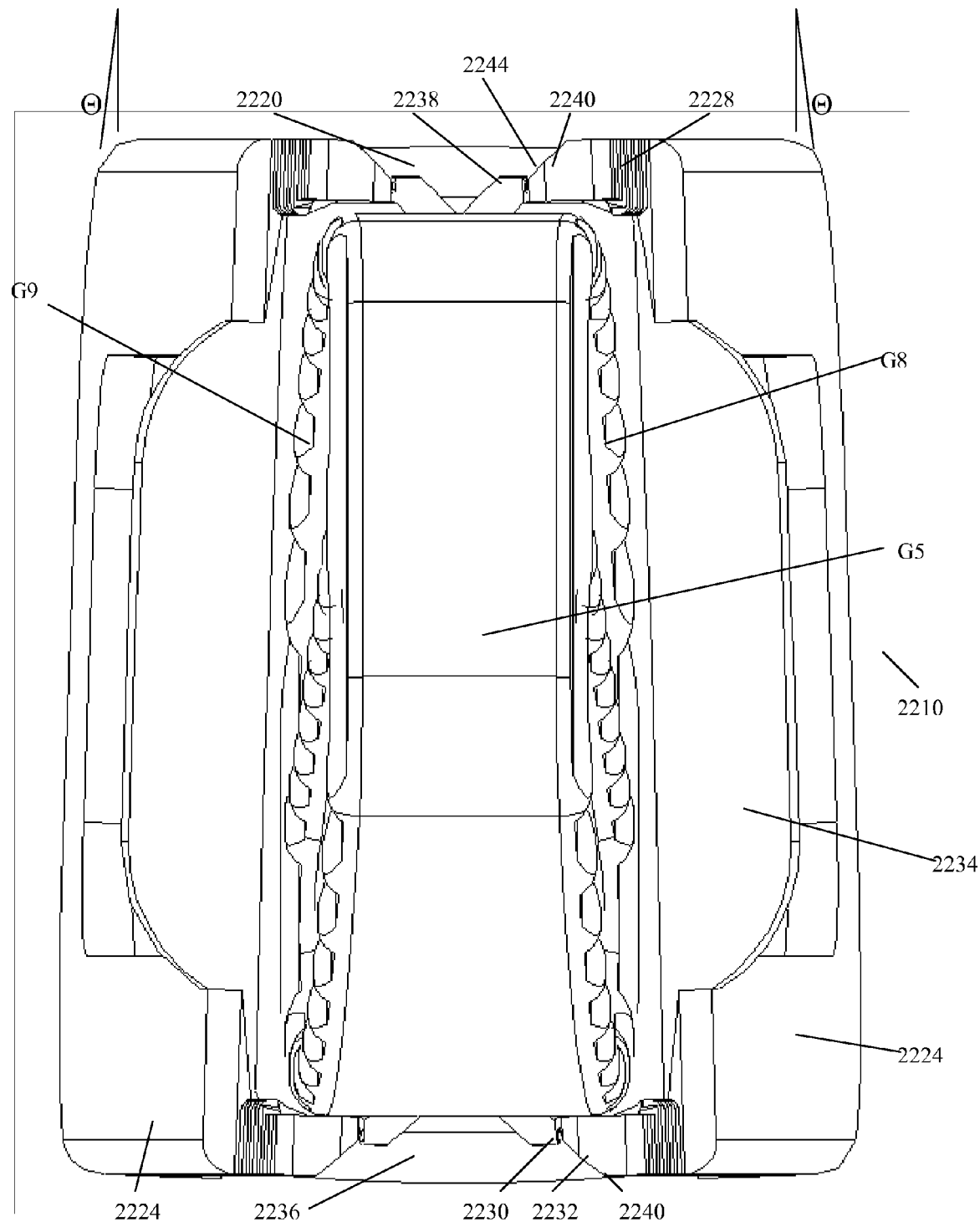
FIG. 23 is an elevational view of the distal end of the insertion instrument and implant of FIG. 22, demonstrating a compound distraction angle suitable for anterior lateral implant insertion, in accordance with one or more embodiments of the present invention.

FIG. 22-26 depict yet another embodiment of the insertion device 2210, in accordance with various aspects of the invention, for placing an implant G5 between two adjacent vertebral bodies V1 and V2 from an anterior-lateral, or oblique, approach. Otherwise stated, the direction of insertion of implant G5 may be at a non-zero angle with respect to the longitudinal axis of the insertion instrument 2210 about an axis perpendicular the planes of the upper and lower surfaces of implant G5. In one or more embodiments, the non-zero angle may be between 10 and 90 degrees. In one or more other embodiments, the non-zero angle may be between 15 and 45 degrees. However, in still other embodiments any non-zero angle between the direction of insertion and the longitudinal axes of insertion instrument 10 may be employed. In one or more embodiments, two distraction guides 2220 and 2236 may be removably mounted to two respective slideable arms 2222. Distraction guides 2220 and 2236 may be shaped and sized to correspond with the size and shape of a particular implant G5 which has been chosen by a surgeon to conform to a particular patient's anatomy. Various implementations of the distraction guides 2220 and 2236 may be made available to match various respective specific implants G5. In one or more alternative embodiments, distraction guides 2220 and 2236 may be designed to enable the implant G5 to be inserted from an anterior-lateral approach while maintaining the appropriate sagittal alignment of the spine. In addition to having the grooves 2238 and 2230 and angled faces 2244 and 2232 propagate in a generally lordotic angle, they are also set at a compound angle, or lateral distraction angle Θ, as shown in FIG. 23. By combining the compound angle Θ with the distraction angle between the longitudinal axes of the ramps 2224, the vertebral bodies may be distracted at the appropriate sagittal angle. The sagittal angle of distraction between the vertebral bodies that may be provided by the above combination may be best seen in FIGS. 25 and 26.

In one or more embodiments, tube 2216 may move along base 2212 employing sliding contact, rolling contact, or other suitable motion interface. Once the tube 2216 is in a desired position with respect to the base 2212, the tube 2216 may be locked into place using a locking arm, such as locking arm 1920 shown in FIG. 19. Motion of the tube 2216 with respect to the base 2212 may be operable to control the position of the slideable arms 2222 and the distraction guides 2220 and 2236. In one or more embodiments, as the tube 2216 moves toward the implant G5, the inside edges of the tube 2216 may engage the angled faces 2248 of the arms 2222, thereby pushing the arms 2222 into a laterally inward position. In one or more embodiments, the implant G5 may be attached to the insertion instrument 2210 by means of an elongated shaft 2214. Shaft 2214 may extend through the entire body 2212 of the insertion instrument 2210. Shaft 2214 may include a threaded tip 2218, at the distal end of shaft 2214, that may thread into the implant G5 by means of a threaded hole G7 on the anterior-lateral face (a face of the implant G5 facing the proximal end of the instrument 2210) of the implant G5.

In one or more embodiments, the distraction guides 2220 and 2236 may be removably attached to the slideable arms 2222. Accordingly, as the arms 2222 move laterally, the distraction guides 2220 and 2236 may move laterally along with the arms 2222. As the distraction guides 2236 move laterally inward, the inner wall 2250 of each distraction guide 2220, 2236 may contact the perimeter of the implant G5 and may thereby operate to hold the implant in place. Once the implant G5 is securely held by the threaded shaft 2214, the ramps 2224 can be slid into position. Because of the compound angle Θ of the grooves 2238 and 2230 and angled faces 2244 and 2232, the ramps 2224 are likewise held at this angle Θ.

Figure 24:
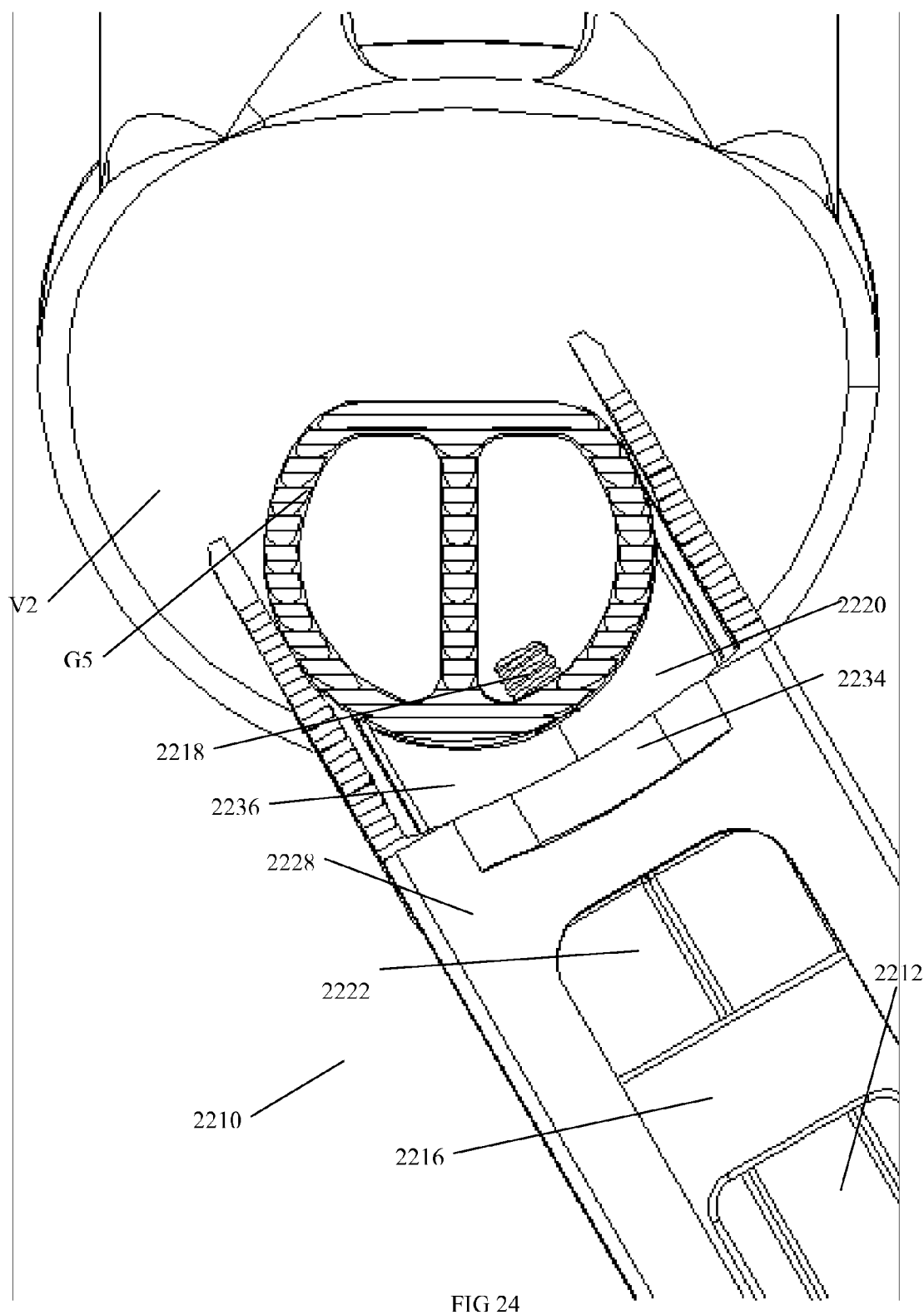
FIG. 24 is a plan view of a portion of the insertion instrument and implant of FIG. 22 along with a vertebral body, depicting an anterior-lateral approach to implant insertion, in accordance with one or more embodiments of the present invention.

FIG. 24 depicts the instrument 2210 and implant G5 on a vertebral body V2 from an anterior lateral approach, in accordance with one or more embodiments of the present invention. It is noted that that the implant G5 may be in the same orientation it would have been in, had the implant G5 been implanted from a straight anterior approach, in which the insertion direction and the longitudinal axis of the insertion instrument 10 are aligned. Proper orientation of the implant during the insertion process may be beneficial in ensuring that the proper sagittal alignment of the spine is maintained during and after insertion of the implant G5. FIG. 24 further shows threaded tip 2218 protruding through the sidewall of the implant G5. As the insertion progresses into the intervertebral cavity above the vertebral body V2, depth stops 2234 of the ramps 2224 may engage the anterior lateral face of the body V2.

Figure 25:
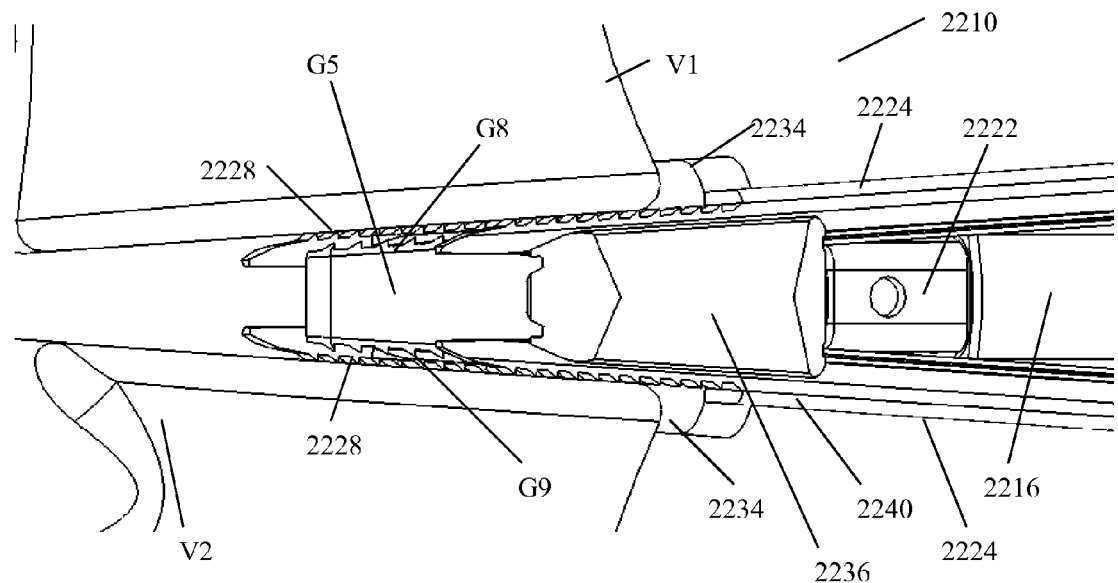
FIG. 25 is an elevational view of a side of the insertion instrument of FIG. 22 employing an anterior-lateral approach to implant insertion, and showing the distraction guide in a final position in relation to the vertebral bodies and the distraction ramps, in accordance with one or more embodiments of the present invention.

FIG. 25 shows the device 2210 in the fully distracted position between the vertebral bodies V1 and V2 with the distraction guide 2236 and the implant G5 fully advanced into the intervertebral cavity. At the insertion stage shown in FIG. 25, the ramps 2224 may be fully distracted. The implant G5 may be located at a desired final location between the adjacent vertebral bodies. The distance between the respective distraction faces 2228 of the two ramps 2224 may be slightly greater than the height of the implant G5, thereby enabling the serrated faces G8 and G9 to be free from contact with the vertebral bodies V1 and V2. Thus, at this stage of the insertion process, implant G5 may still not have experienced any compressive force from the vertebral bodies. Furthermore, due to the combination of the angle of distraction of the longitudinal axes of the ramps 2224 and the compound angle Θ, the ramps 2224 may be distracted while being maintained at a constant sagittal angle with respect to one another. It is noted that that the combination of these angles may match the lordotic angle between the upper and lower contact surfaces of implant G5 as well.

Figure 26:
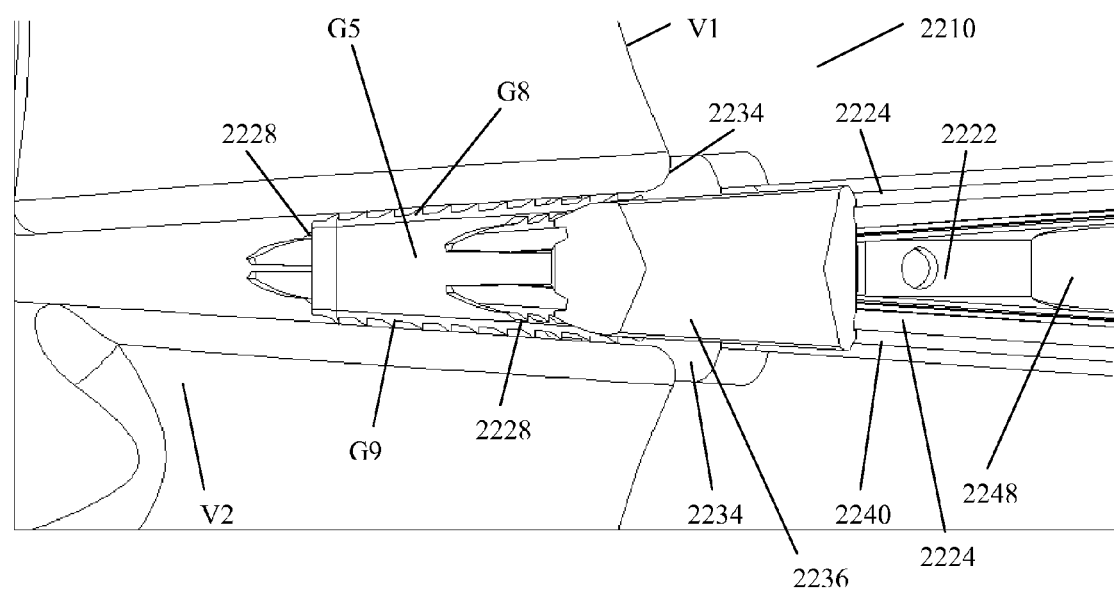
FIG. 26 is an elevational view of a side of the insertion instrument of FIG. 25, showing the engagement of an implant having a height greater than the combined height of the distraction ramps and the guides, in accordance with one or more embodiments of the present invention.

FIG. 26 demonstrates the final positioning of the implant G5 and the release of the implant G5 by the instrument 2210, in accordance with one or more embodiments of the present invention. With the implant G5 in the desired position in relation to the vertebral bodies V, the tube 2216 may be retracted with respect to the body 2212 of instrument 2210. As the tube 2216 is retracted, internal springs may cause the arms 2222 to move out laterally, which may in turn cause the distraction guides 2220 and 2236 to move out laterally as well. The outward lateral motion of the distraction guides 2220 and 2236 may cause the distraction guides 2220 and 2236 to stop receiving, or otherwise stated, to stop resisting the compressive force imparted by the adjacent vertebral bodies V1 and V2. Thus, as the guides 2220 and 2236 move out laterally, the compressive force from the adjacent bodies V1 and V2 may cause the ramps 2224 to approach one another, thereby enabling the vertebral bodies V1 and V2 approach one another as well. Because the angled faces 2240 of the ramps 2224 may rest upon the corresponding angled faces 2232 and 2244 of the distraction guides 2220 and 2236, respectively, the ramps 2224 may comply with the compressive force from the adjacent bodies and move into the expanding space between the laterally displaced distraction guides 2220 and 2236. The approach of the ramps toward one another may continue until the distance between the outer surfaces 2228 of the ramps 2224 is less than the height of the implant G5. As the distraction distance between the vertebral bodies V1 and V2 diminishes, the compressive force urging the bodies V1 and V2 together may be gradually transferred from the ramps 2224 to the implant G5. In one or more embodiments, the serrated faces G8 and G9 of the implant G5 may engage, or bite into, the endplates (the implant-facing surfaces) of the vertebral bodies V1 and V2. The above-described gradual transfer of compressive force may enable the implant G5 to remain in a desired final location between the bodies V1 and V2 without being unintentionally dislodged by the extraction of the insertion instrument 2210. In one or more embodiments, the shaft 2214 may be unthreaded from the implant hole G7. Upon completion of the above-listed steps, insertion instrument 2210 may be removed from the interbody cavity with the implant G5 located in the desired position with respect to the vertebral bodies V. As discussed in connection with another embodiment herein, various characteristics of insertion instrument 2210 may enable instrument 2210 to be free of any compressive force from the bodies V1 and V2 during the extraction thereof from the interbody cavity (in this case, an intervertebral cavity).

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. An instrument for inserting an implant, comprising:
   a first ramp including a vertebral contact surface and opposing lateral edges, each extending parallel to a first longitudinal axis between proximal and distal ends thereof;
   a second ramp including a vertebral contact surface and opposing lateral edges, each extending parallel to a second longitudinal axis between proximal and distal ends thereof; and
   at least one distraction guide including: (i) first and second faces directed medially toward one another, and each including first and second engagement structures slidingly engaging a respective one of the lateral edges of the first and second ramps such that an initial angle is established between the first and second longitudinal axes, and (ii) an implant clamping structure for engaging the implant during insertion, wherein:
   advancement of the distraction guide, and the implant engaged therewith, distally results in sliding of the first and second engagement structures of each of the first and second faces along the respective lateral edges of the first and second ramps and parallel to respective ones of the first and second longitudinal axes such that the respective vertebral contact surfaces of the first and second ramps separate while holding the initial angle substantially constant.

2. The insertion instrument of claim 1, wherein the initial angle is a non-zero angle.

3. The insertion instrument of claim 1, wherein the first and second engagement structures of each of the first and second faces extends along respective longitudinal edges thereof, and the longitudinal edges of each of the first and second faces are oriented at the initial angle with respect to one another.

4. The insertion instrument of claim 3, wherein:
   each of the lateral edges of the first and second ramps includes an angled surface laying in a plane transverse a respective one of the vertebral contact surfaces; and
   each of the first and second engagement structures of the first and second faces includes a correspondingly angled surface engaging a respective one of the angled surfaces of the first and second ramps,
   wherein each of the angled surfaces engages and slides with respect to a respective one of the correspondingly angled surfaces such that a compressive load urging the first and second vertebral contact surfaces toward one another is transferred through the angled and correspondingly angled surfaces to the distraction guide during sliding.

5. The insertion instrument of claim 4, wherein the angled and correspondingly angled surfaces are at an angle of about 45 degrees with respect to an associated one of the vertebral contact surfaces.

6. The insertion instrument of claim 1, wherein the separation of the first and second ramps, while maintaining the initial angle therebetween substantially constant, operates to provide parallel distraction of adjacent bodies when the insertion instrument is positioned within an interbody cavity.

7. The insertion instrument of claim 1, wherein each of the vertebral contact surfaces are sized and shaped to engage adjacent vertebral bodies of an intervertebral cavity.

8. The insertion instrument of claim 7, wherein the at least one distraction guide is configured to accommodate the implant for insertion into the intervertebral cavity.

9. The insertion instrument of claim 8, wherein the distraction guide is configured to receive a compressive force imparted by the intervertebral cavity on the first and second ramps, thereby avoiding loading the implant with the compressive force during insertion of the instrument into the intervertebral cavity.

10. The insertion instrument of claim 9, wherein the distraction guide operates to discontinue receiving the compressive force imparted by the intervertebral cavity once the implant insertion is complete, thereby transferring the compressive force to the implant.

11. The insertion instrument of claim 1, wherein the at least one distraction guide operates to move laterally with respect to the first and second longitudinal axes of the first and second ramps.

12. The insertion instrument of claim 11, wherein a geometric interface between the distraction guide and the first and second ramps is configured such that the lateral motion of the distraction guide enables the first and second ramps to approach one another in response to a compressive force acting upon the first and second ramps.

13. The insertion instrument of claim 12, wherein the geometric interface comprises at least one angled surface along a longitudinal edge of at least one of the first and second faces of the distraction guide.

14. The insertion instrument of claim 13, wherein the geometric interface further comprises at least one angled surface along a longitudinal edge of at least one of the first and second ramps that engages the angled surface on the distraction guide.

15. The insertion instrument of claim 10, wherein the discontinuation of receipt of the compressive force by the distraction guide operates to cause the first and second ramps to reduce a separation distance therebetween in response to the compressive force.

16. The insertion instrument of claim 15, wherein the separation distance between the first and second ramps is reduced such that the distance between the outer surfaces of the first and second ramps is less than the thickness of the implant.

17. The insertion instrument of claim 16, wherein the first and second ramps operate to reduce the separation distance therebetween without contacting the implant.

18. The insertion instrument of claim 17, wherein at least one of the first and second ramps comprises at least one finger portion that is configured to move along a side of the implant without contacting the implant as the separation distance between the first and second ramps is reduced.

19. The insertion instrument of claim 16, wherein the reduction in the distance between the first and second ramps enables removal of the insertion instrument from the intervertebral cavity in the absence of compressive force on the first and second ramps from the intervertebral cavity.

20. The insertion instrument of claim 1, wherein the distraction guide includes engagement elements having dimensions corresponding to those of the implant.

21. The insertion instrument of claim 20, wherein the engagement elements includes a plurality of grasping jaws for grasping the implant within the insertion instrument.

22. The insertion instrument of claim 1, wherein advancement of distraction guide, and the implant engaged therewith, proximally permits sliding the respective vertebral contact surfaces of the first and second ramps past the distraction guide and the implant in a distal direction.

* * * * *